US012655092B2

(12) United States Patent
Zaitoon et al.

(10) Patent No.: US 12,655,092 B2
(45) Date of Patent: Jun. 16, 2026

(54) PRECURSOR COMPOUNDS OF ESTER COMPOUNDS

(71) Applicant: University of Guelph, Guelph (CA)

(72) Inventors: Amr Zaitoon, Guelph (CA); Loong-Tak Lim, Guelph (CA); Cynthia Scott-Dupree, Fergus (CA)

(73) Assignee: UNIVERSITY OF GUELPH, Guelph (CA)

( * ) Notice: Subject to any disclaimer, the term of this patent is extended or adjusted under 35 U.S.C. 154(b) by 1225 days.

(21) Appl. No.: 17/614,357

(22) PCT Filed: May 28, 2020

(86) PCT No.: PCT/CA2020/050725
§ 371 (c)(1),
(2) Date: Nov. 25, 2021

(87) PCT Pub. No.: WO2020/237378
PCT Pub. Date: Dec. 3, 2020

(65) Prior Publication Data

US 2022/0220067 A1 Jul. 14, 2022

Related U.S. Application Data

(60) Provisional application No. 62/855,255, filed on May 31, 2019.

(51) Int. Cl.
*C07C 251/74* (2006.01)
*C07C 243/28* (2006.01)

(52) U.S. Cl.
CPC .......... *C07C 251/74* (2013.01); *C07C 243/28* (2013.01)

(58) Field of Classification Search
None
See application file for complete search history.

(56) References Cited

PUBLICATIONS

Azizi et al. (Strut. Chem., 2017, 28:687-695) (Year: 2017).*
Kocevar et al. (Synlett, 1995(3), 241). (Year: 1995).*
Herrmann, A. Controlled release of volatiles under mild reaction conditions from nature to everyday products. Angewandte Chemie International Edition Verlag Chemie. 46(3):5836-5863, 2007.
Levrand, Barbara et al. Controlled Release of Volatile Aldehydes and Ketones from Dynamic Mixtures Generated by Reversible Hydrazone Formation. Helvetica Chimica Acta, Verlag Helvetica Chemica Acta. 90(12):2291-2314, 2007.
European Search Report dated Nov. 30, 2022.
ASTM Standard E104-02. 2012. "Standard Practice for Maintaining Constant Relative Humidity by Means of Aqueous Solutions." Www.Astm.Org. https://doi.org/10.1520/E0104-02R12.
Bessi, Haithem, Sihem Bellagha, Kaouthar Grissa Lebdi, Veronique Bikoba, and Elizabeth J. Mitcham. 2015. "Ethyl Formate Fumigation of Dry and Semidry Date Fruits: Experimental Kinetics, Modeling, and Lethal Effect on Carob Moth." Journal of Economic Entomology. https://doi.org/10.1093/jee/tov032.
Bolin, HR, AD King Jr, WL Stanley, and L Jurd. 1972. "Antimicrobial Protection of Moisturized Deglet Noor Dates." Applied and Environmental Microbiology.
Damcevski, K.A. ans Annis, P.C. 2006. Influnce of grain and relative humidity on the mortality of *Sitophilusorzae*(L.) adults exposed to ethyl formate vapour. J. Stored Products Res.42:61-74.
Desmarchelier, J M. 1999. "Ethyl Formate and Formic Acid: Occurrence and Environmental Fate." Postharvest News and Information 10: 7-12.
Greenspan, Lewis. 1977. "Humidity Fixed Points of Binary Saturated Aqueous Solutions." Journal of Research of the National Bureau of Standards Section A: Physics and Chemistry. https://doi.org/10.6028/jres.081A.011.
Learmonth, Stewart, YongLin Ren, Manjree Agarwal, James Newman, Hui Cheng, and John Sutton. 2012. "Evaluation of Ethyl Formate & Nitrogen for the Disinfestation of Eucalyptus Weevils on Export Apples." Department of Agriculture & Food, Western Australia,Murdoch University, Horticulture Australia Ltd PN#AP09045.
Lee, Laurence, Joseph Arul, Robert Lencki, and Francois Castaigne. 1995. "A Review on Modified Atmosphere Packaging and Preservation of Fresh Fruits and Vegetables: Physiological Basis and Practical Aspects—Part I." Packaging Technology and Science.
Jash, A. et al.: "Activated release of bioactive aldehydes from their precursors embedded in electrospun poly(lactic acid) nonwovens". RSC Advances, vol. 8, pp. 19930-19938, 2018.
Sancak, K. et al.: "Synthesis, characterization, and antioxidant activities of new trisubstituted triazoles". Turkish Journal of Chemistry, vol. 36(3), pp. 457-466, 2012.
Petersen, Karina, Per Væggemose Nielsen, Grete Bertelsen, Mark Lawther, Mette B. Olsen, Nils H. Nilsson, and Grith Mortensen. 1999. "Potential of Biobased Materials for Food Packaging." Trends in Food Science and Technology. https://doi.org/10.1016/S0924-2244(99)00019-9.
Ragaert, P., F. Devlieghere, and J. Debevere. 2007. "Role of Microbiological and Physiological Spoilage Mechanisms during Storage of Minimally Processed Vegetables." Postharvest Biology and Technology. https://doi.org/10.1016/j.postharvbio.2007.01.001.
Ren, Yong Lin, and Daphne Mahon. 2006. "Fumigation Trials on the Application of Ethyl Formate to Wheat, Split Faba Beans and Sorghum in Small Metal Bins." Journal of Stored Products Research. https://doi.org/10.1016/j.jspr.2005.04.002.

(Continued)

*Primary Examiner* — Renee Claytor
*Assistant Examiner* — Jennifer C Sawyer
(74) *Attorney, Agent, or Firm* — Smart & Biggar LP; Patricia Folkins

(57) ABSTRACT

The present disclosure relates to compounds of the formula (I) which are precursor compounds of esters, whereby upon hydrolysis of the precursor compound, an ester compound is released. This ester precursor approach can be useful for applications where controlled release of, for example, ethyl formate, is beneficial.

(I)

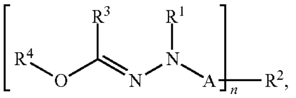

13 Claims, 14 Drawing Sheets

(56) References Cited

PUBLICATIONS

Schafer, K.S. 1999. "Methyl bromide phase-out strategies: A global compilation of the laws and regulations". United Nations Environment program.
Simpson, T, V Bikoba, C Tipping, and E J Mitcham. 2007. "Ethyl Formate as a Postharvest Fumigant for Selected Pests of Table Grapes." Journal of Economic Entomology. https://doi.org/10.1603/0022-0493(2007)100[1084:EFAAPF] 2.0.CO;2.
Simpson, Tiffanie, Veronique Bikoba, and Elizabeth J. Mitcham. 2004. "Effects of Ethyl Formate on Fruit Quality and Target Pest Mortality for Harvested Strawberries." Postharvest Biology and Technology 34 (3): 313-19. https://doi.org/10.1016/j.postharvbio.2004.05.015.
Utama, I. Made S., Ron B.H. Wills, Shimshon Ben-Yehoshua, and Clem Kuek. 2002. "In Vitro Efficacy of Plant Volatiles for Inhibiting the Growth of Fruit and Vegetable Decay Microorganisms." Journal of Agricultural and Food Chemistry. https://doi.org/10.1021/jf020484d.
Zaitoon, A. et al.: "Synthesis and Characterization of Ethyl Formate Precursor for Activated Release Application" Journal of Agricultural and Food Chemistry, vol. 67, pp. 13914-13921, Nov. 22, 2019 *the whole document*.
Saied, T. et al.: "Reduction Electrochimique Directe et Indirecte des N-arylsulfonyl-N-phenyl Hydrazonates". Journal de la Societe Chimique de Tunisie, vol. 4(12), pp. 1649-1656, 2002.
Kosmrlj, B. et al.: "Transformations of Hydrazine Derivatives. Ethoxymethylene Hydrazones as Powerful Reagents in Organic Synthesis". Acta Chimica Slovenica, vol. 43(2), pp. 153-162, 1996.
McDonald, R. M. et al.: "A Convenient Synthesis of Ester p-Tosylhydrazones and Studies of the Thermal Decomposition of Some of Their Sodium Salts" Journal of Organic Chemistry, vol. 31, pp. 488-494, 1966.
Kacem, Y. et al.: "A new procedure for the synthesis of 4-substituted-2H-1,2,3-benzo-thiadiazine 1, 1-dioxides via directed ortho-lithiation of N'-arylsulfonylhydrazonates". Tetrahedron Letters, vol. 54, pp. 4023-4025, 2013.
Williard, P. G. et al.: "N-aryl sulfonyl hydrazimidates—hydrazones of esters". Tetrahedron Letters, vol. 22, pp. 2731-2734, 1981.
Zribi, F. et al.: "Proprietes Chimiques des Hydrazonates : Action des Organomagnesiens sur les Hydrazonates Simple, N-1-acyles et N-1-ethoxycarbonyles". Journal de la Societe Chimique de Tunisie, vol. 4(9), pp. 971-976, 2001.
Chaioui, M. et al.: "Preparation de N-aminotriazolones et de N-aminotriazoles a partir d'hydrazonates" Comptes Rendus des Seances de l'Academie des Sciences, Serie 2: Mecanique-Physique, Chimie, Sciences de l'Univers, Sciences de la Terre, vol. 293(8), pp. 573-576, 1981.
Jacobsen, P. et al.: "N-Sulfonylformamidrazones; Preparation and Structure". Tetrahedron, vol. 38(3), pp. 369-372, 1982.
Peet, N. P. et al.: "Synthesis of 3-Methyl-[ 1,2,4]-triazepino [ 6,5,4-jk] carbazol-4(3H)one". Journal of Heterocyclic Chemistry, vol. 14, pp. 1147-1150, 1977.
Ltnlver, D. et al.: "Novel 1,2,4-Triazole Derivatives: Structure, DFT Study, X-Ray Analysis, and Antimicrobial Activity". Russian Journal of Organic Chemistry, vol. 55(2), pp. 254-261, Feb. 2019.
Azizi, A. et al.: "The X- . . . benzohydrazide complexes: the interplay between anion-rc and H-bond interactions" Structural Chemistry, vol. 28, pp. 687-695, 2017.
Kocevar, M. et al.: "A General and Simple Approach to N'-Acylformamidrazones". Synlett, issue 3, pp. 241-242, 1995.
Ainsworth, C. et al.: "Alkyl-1,3,4-oxadiazoles". Journal of Organic Chemistry, vol. 31, pp. 3442-3444, 1966.

* cited by examiner

PRECURSOR COMPOUNDS OF ESTER COMPOUNDS

CROSS-REFERENCE TO RELATED APPLICATIONS

This application is a U.S. national phase entry of PCT/CA2020/050725, filed May 28, 2020 which claims the benefit of priority to U.S. Provisional Application No. 62/855,255, filed May 31, 2019, the contents of which are incorporated herein by reference in their entirety.

FIELD

The present disclosure relates to compounds of the formula (I) which are precursor compounds of esters, whereby upon hydrolysis of the precursor compound, an ester compound is released.

INTRODUCTION

Ester compounds have many uses in industry, including fumigation, food preservation, flavoring, perfumery and other applications. However, due to their volatility, their end use can be challenging. For example, ethyl formate (EF) has relatively high vapor pressure (200 mmHg at 20° C.) and high flammability. Moreover, it is susceptible to hydrolytic degradation in the presence of water to formic acid and ethanol. Therefore, the compound needs to be stabilized to prevent its premature release and degradation.

To prevent the introduction of invasive insect species that can be detrimental to the environment and crops, many jurisdictions have established directives that mandate fruit and vegetable importers to produce phytosanitary certificate declaring that their shipments are free of specific insect pests and/or demonstrating proof of treatment, such as fumigation with methyl bromide (MB). While MB is very effective for this purpose, it is highly toxic and is classified as class 1 ozone depleting substance that poses significant environmental threat. Signatories of Montreal Protocol are committed to reduce and eventually phase phase-out the use of MB (Schafer, 1999). In California, under "critical use exemption", EPA has been granting the use of MB in soil fumigation to eliminate pests before planting new crops, although 2016 was the last year that strawberries growers in California are allowed to use MB as a soil fumigant. Recognizing the environmental impact and toxicity of MB, many agencies (e.g., the United Nations, Canada Food Inspection Agency, US Environmental Protection Agency) encourage commodities and fruits producers to use alternative fumigants and other strategies to address pest issues.

EF is a US Food and Drug Administration approved food-flavouring agent with a Generally Recognized as Safe status. It is a volatile compound naturally occurring in many products (e.g., rice, beef, grapes, wine, beer, and cheese). Studies have shown EF is an effective fumigant for destroying insects in various crops. For example, Simpson et al. (2004, 2007) demonstrated that EF concentrations ranging from 0.8 to 4.7% are effective to induce various degrees of mortality in flower thrip, two-spotted spider mite, mealybugs, and an omnivorous leafroller on strawberries and grapes. Bessi et al. (2016) reported treatment of date fruits with EF at 143 $g/m^3$ headspace concentration for 2 h, which resulted in 98 to 100% mortality rate on carob moth without causing significant changes in fruit quality. Another study showed that EF fumigation of apple at 50-55 $g/m^3$ headspace concentration at 4-8° C. for 24 h resulted in 100% mortality of adult weevils without affecting the quality and shelf-life (Learmonth and Ren, 2012). Ren and Mahon (2006) evaluated the efficacy of EF for insect control of wheat, split faba beans, and sorghum stored in unsealed metal beans using a two-exposure approach (85 g/t for 4 h followed by the second 85 g/t treatment). They reported high level of control of all stages of most of the test insects in the wheat, split faba beans and sorghum bins. Utama et al. studied the antimicrobial activities of EF vapor on a selected fruit and vegetable decay microorganisms grown in an agar medium (Utama et al., 2002). They reported that EF with a concentration of 6.5-11.5 mmol/dish was germicidal against the growth of *Rhizopus stolonifer, Colletotrichum musae, Erwinia carotovora*, and *Pseudomonas aeruginosa*, but did not show complete inhibit of *Penicillium digitatum* growth. Bolin et al. reported that EF at 3 mL/lb was able to inhibit the microbial growth of *Saccharomyces rouxii* and *Saccharomyces mellis* on Deglet Noor dates (Bolin et al., 1972). Thus, EF's insecticidal and antimicrobial properties can be useful for active packaging applications.

Unlike other fumigants, such as MB and phosphine, EF degrades rapidly and does not pose long-term residual concerns (Desmarchelier et al., 1999). The hydrolytic by-products formed, formic acid and ethanol, are both naturally occurring and exhibit antimicrobial properties. Damcevski and Annis (2006) reported that relative humidity can influence the efficacy of EF on the mortality of *Sitophilus oryzae* adults; the higher the relative humidity, the lower the dosage required to achieve 99% mortality. Therefore, the application of EF for the fumigation of fresh fruits and vegetables can be enhanced under elevated relative humidity conditions. Due to its high vapor pressure and to suppress its flammability, EF has been mixed with $CO_2$ in a compressed gas cylinder, at 16.7% wt. level, for fumigation of fruits, vegetables, and grains. The product is commercially available as Vapormate® by Linde Group. Nonetheless, compressed gas cylinders are inconvenient to transport and bulky for storage. Moreover, end-use of the gas mixture requires pressure regulator and metering devices to ensure safety and accurate dosage of the fumigant.

SUMMARY

To address these issues, the present disclosure describes a solid-state ester precursor approach, which can be useful for applications where controlled release of, for example, EF is beneficial. For example, in-package fumigation of fruits and vegetables with EF to destroy invasive insects and microorganisms during distribution could avoid the handling of large quantities of fumigant in enclosed spaces, thereby making the treatment more cost-effective and reducing unwanted release of EF into the environment.

Accordingly, in one embodiment, the present disclosure relates to compounds of the formula (I) which are precursors of ester compounds (I)

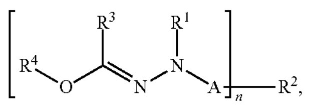

wherein

A is C═O, C═S, —S($O_2$)—, or —C═N—R, wherein R is $C_1$-$C_5$-alkyl;

$R^1$ is H, $C_1$-$C_5$-alkyl, or phenyl;

$R^2$ is a mono-, di-, tri- or tetra $C_1$-$C_{18}$-hydrocarbyl radical which is linear, branched, cyclic, or aromatic, or combination thereof;

$R^3$ is H or $C_1$-$C_3$-alkyl;

$R^4$ is $C_1$-$C_5$-alkyl or $C_6$-$C_{10}$-aryl;

n is the integer 1, 2, 3, or 4.

Upon hydrolysis, the precursor compounds of formula (I) release an ester compound of the formula (II)

(II)

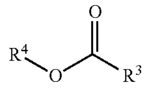

wherein $R^3$ and $R^4$ are as defined above.

The present disclosure also includes a process for the preparation of the precursor compounds of formula (I).

In certain embodiments, the present disclosure includes a use of the precursor compounds of formula (I) for the release of EF as a fumigant for killing pests and/or insects on fresh foods, such as fruits and vegetables. In other embodiments, the present disclosure further includes a method for controlling, reducing or killing an infestation of pests on fresh food, such as fruits and vegetables, the method comprising subjecting the precursor compound of the formula (I) to hydrolytic conditions to release EF in the presence of the food, and wherein the EF prevents, controls, reduces or kills the infestation.

In other embodiments, the present disclosure also includes encapsulating the precursor compounds of formula (I) into carriers, such as nonwovens, films, coatings, particles, capsules, foams, composite structures, and so on, wherein, upon contact with an acid, the encapsulated precursor compound of formula (I) releases EF within the package to prevent, control, reduce or kill a pest or insect infestation.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

BRIEF DESCRIPTION OF THE DRAWINGS

The present disclosure will now be described in greater detail with reference to the drawings in which.

DESCRIPTION OF VARIOUS EMBODIMENTS

(I) Definitions

Figure 1:
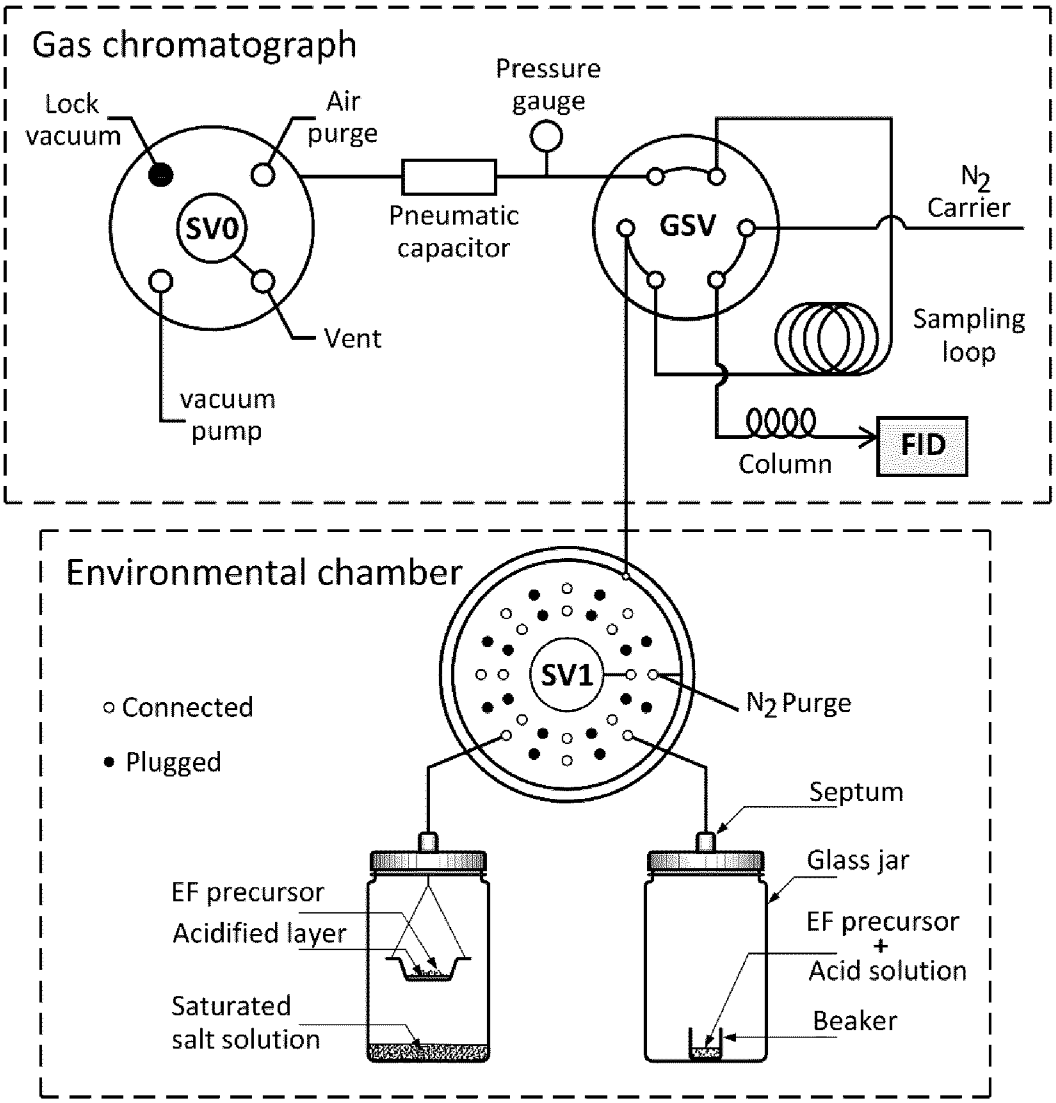
FIG. 1 is a schematic representation of an automatic headspace analysis system for studying easter release kinetics. GSV; gas sampling valve. SV0 and SV1; stream selection valves.

The term "$C_1$-$C_{18}$-hydrocarbyl radical" as used herein refers to a group having a carbon atom directly attached to the remainder of the molecule and having a predominantly hydrocarbon character having between 1 and 18 carbon atoms. The hydrocarbyl group may be aliphatic (alkyl, alkenyl, alkylene), alicyclic (cycloalkyl, cycloalkenyl, cycloalkylene), aromatic, or a combination thereof, and be attached at 1, 2, 3 or 4 different location to the remainder of the molecule depending on the value of the variable "n".

The term "$C_1$-$C_x$-alkyl group" according to the present disclosure refers to alkyl groups having 1 to X carbon atoms. $C_1$-$C_5$-alkyl, for example includes, among others, methyl, ethyl, n-propyl, iso-propyl, n-butyl, iso-butyl, sec-butyl, tert-butyl, n-pentyl, iso-pentyl, sec-pentyl, tert-pentyl, neo-pentyl, and the like.

The term "$C_1$-$C_x$-alkylene group" according to the present disclosure refers to alkylene groups having 1 to X carbon atoms, divalent, trivalent or tetravalent hydrocarbon radicals having straight, branched or cyclic moieties or combinations thereof. $C_1$-$C_5$-alkylene, for example includes, among others, methylene, ethylene, n-propylene, and the like.

The term “hydrolytic conditions” as used herein refers to any condition which can hydrolytically cleave the precursor compounds of the formula (I) into constituent compounds including the ester compounds of the formula (II).

The term “control,” as used herein referring to an infestation of pests, means killing or inhibiting the growth of any pest, such as flower thrips, two-spotted spider mites, mealybugs, omnivorous leafrollers etc., by killing, reducing in numbers, and/or reducing growth, of the pest.

(II) Precursor Compounds of the Formula (I)

Ester compounds are well known in industry for fumigation, food preservation, flavoring, perfumery and other applications. However, due to their volatility, the end use of esters can be challenging. The present disclosure relates to precursor compounds of the formula (I), which upon being exposed to hydrolytic conditions, release the ester compound.

Accordingly, in one embodiment, the present disclosure relates to compounds of the formula (I) which are precursors of ester compounds (II):

(I)

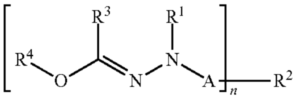

wherein

A is C═O, C═S, —S($O_2$)—, or —C═N—R, wherein R is H or $C_1$-$C_5$-alkyl (H or $CH_3$);

$R^1$ is H, $C_1$-$C_5$-alkyl, or phenyl;

$R^2$ is a mono-, di-, tri- or tetra $C_1$-$C_{18}$-hydrocarbyl radical which is linear, branched, cyclic or aromatic, or a combination thereof;

$R^3$ is H or $C_1$-$C_3$-alkyl;

$R^4$ is $C_1$-$C_5$-alkyl or $C_6$-$C_{10}$-aryl;

n is the integer 1, 2, 3, or 4.

In another embodiment, upon being exposed to hydrolytic conditions, the precursor compounds of formula (I) release an ester compound of the formula (II):

(II)

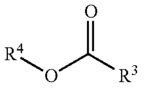

wherein $R^3$ and $R^4$ are as defined above, whereby the hydrazide moiety in the compounds of formula (I) is hydrolyzed to form the ester compound of formula (II). In another embodiment, the hydrolysis also results in the following compound of the formula (A):

(A)

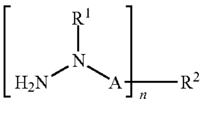

In one embodiment, A is C═O.

In another embodiment, $R^1$ is H, $C_1$-$C_3$-alkyl, or phenyl. In another embodiment, $R^1$ is H, or $C_1$-$C_3$-alkyl. In another embodiment, $R^1$ is H.

In another embodiment, $R^2$ is a mono-, di-, tri- or tetra $C_1$-$C_{18}$-hydrocarbyl radical which is linear, branched, cyclic, or aromatic, or a combination thereof.

In one embodiment, $R^2$ is a $C_1$-$C_{18}$-alkyl, $C_1$-$C_{18}$-alkylene, phenyl, phenylene, $C_1$-$C_{18}$-alkylenephenyl or $C_1$-$C_{18}$-alkylenephenylene.

In one embodiment, $R^2$ is a mono-substituted $C_1$-$C_{18}$-hydrocarbyl radical, n is 1, and the precursor compound of formula (I) has the structure (IA):

(IA)

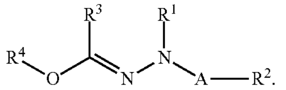

In one embodiment, when n is 1 and $R^2$ is mono-substituted, $R^2$ is a $C_1$-$C_{18}$-alkyl group or a $C_1$-$C_6$-alkyl-phenyl group. In one embodiment, $R^2$ is a $C_1$-$C_6$-alkyl group or a $C_1$-$C_3$-alkyl-phenyl group. In another embodiment, $R^2$ is a $C_1$-$C_3$-alkyl group or —$CH_2$— phenyl. In another embodiment, $R^3$ is H or $C_1$-$C_3$-alkyl, or H and —$CH_3$. In another embodiment, $R^4$ is $C_1$-$C_3$-alkyl, or —$CH_2$—$CH_3$ or —$CH_3$.

In one embodiment, the precursor compound of formula (IA) is

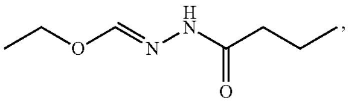

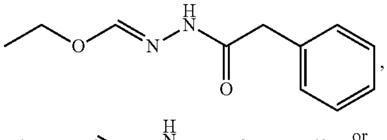

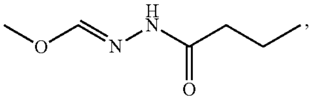

or

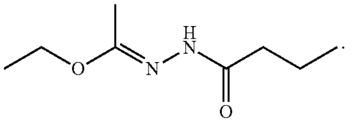

In one embodiment, when $R^2$ is a di-substituted $C_1$-$C_{18}$-hydrocarbyl radical, n is 2, and the precursor compound of formula (I) has the structure (IB):

(IB)

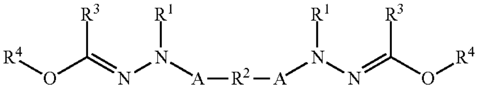

In one embodiment, when n is 2 and $R^2$ is mono-substituted, $R^2$ is a $C_1$-$C_{10}$-alkylene group or alkenylene group, or $R^2$ is a $C_4$-$C_{10}$-alkylene group or alkenylene group, or $R^2$ is a $C_6$-$C_{10}$-alkylene group or alkenylene group. In another embodiment, $R^3$ is H or $C_1$-$C_3$-alkyl, or H and —$CH_3$. In another embodiment, $R^4$ is $C_1$-$C_3$-alkyl, or —$CH_2$—$CH_3$ or —$CH_3$.

In another embodiment, the compound of formula (IB) is

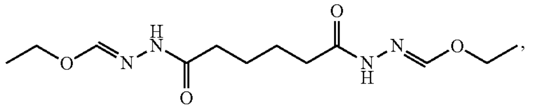

, or

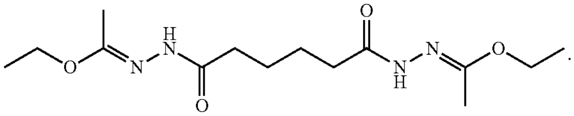

In one embodiment, when $R^2$ is a tri-substituted $C_1$-$C_{18}$-hydrocarbyl radical, n is 3, and the precursor compound of formula (I) has the structure (IC):

(IC)

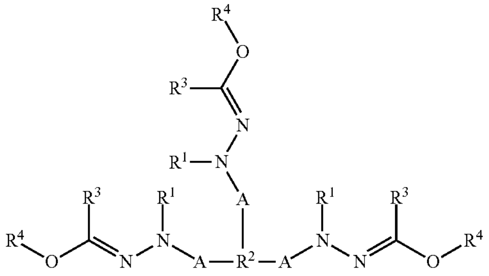

In one embodiment, when $R^2$ is a tetra-substituted $C_1$-$C_{18}$-hydrocarbyl radical, n is 4, and the precursor compound of formula (I) has the structure (ID):

(ID)

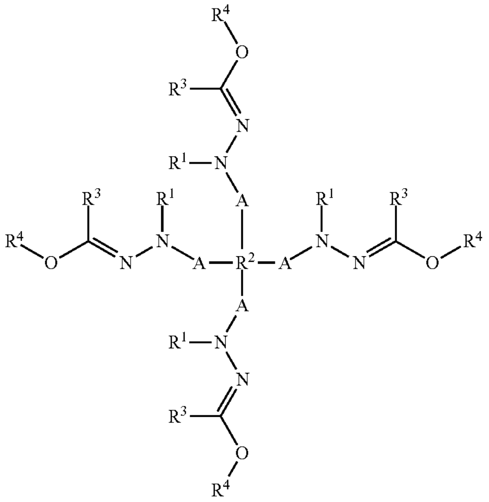

In another embodiment, $R^3$ is H.

In another embodiment, $R^4$ is $C_1$-$C_5$-alkyl or phenyl. In another embodiment, $R^4$ is $C_1$-$C_5$-alkyl. In a further embodiment, $R^4$ is methyl or ethyl.

In another embodiment of the disclosure, upon being exposed to hydrolytic conditions, the precursor compounds of the formula (I) release ester compounds of the formula (II)

(II)

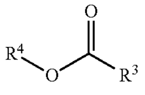

wherein $R^3$ is H or $C_1$-$C_3$-alkyl; and $R^4$ is $C_1$-$C_5$-alkyl or $C_6$-$C_{10}$-aryl.

In another embodiment, the ester compound of the formula (II) is EF:

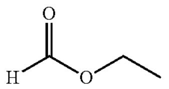

In another embodiment, the hydrolytic conditions comprise exposing the precursor compounds of the formula (I) to conditions which are able to hydrolyze the hydrazide moiety. In another embodiment, the hydrolytic conditions include exposing the precursor compounds of the formula (I) to an acid, moisture or increased temperature. In one embodiment, the acid is a weak acid such as citric acid, acetic acid, formic acid, lactic acid, and so on. In another embodiment, the acid is a gas such as carbon dioxide which forms carbonic acid upon combination with water.

In another embodiment, the precursor compound of the formula (I) is a precursor compound of the formula (III):

(III)

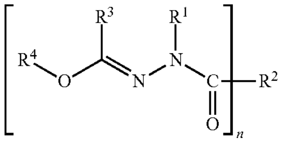

wherein $R^1$ is H, $C_1$-$C_5$-alkyl, or phenyl;

$R^2$ is a mono-, di-, tri- or tetra $C_1$-$C_{18}$-hydrocarbyl radical which is linear, branched or cyclic;

$R^3$ is H or $C_1$-$C_3$-alkyl;

$R^4$ is $C_1$-$C_5$-alkyl or $C_6$-$C_{10}$-aryl;

n is the integer 1, 2, 3, or 4.

In another embodiment, $R^1$ is H, $C_1$-$C_3$-alkyl, or phenyl. In another embodiment, $R^1$ is H, or $C_1$-$C_3$-alkyl. In another embodiment, $R^1$ is H.

In another embodiment, $R^2$ is a mono-, di-, tri- or tetra $C_1$-$C_{18}$-hydrocarbyl radical which is linear, branched or cyclic, wherein when $R^2$ is a mono-substituted $C_1$-$C_{18}$-hydrocarbyl radical, n is 1, and the precursor compound of formula (III) has the structure (IIIA):

(IIIA)

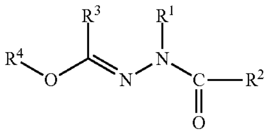

In one embodiment, when n is 1 and $R^2$ is mono-substituted, $R^2$ is a $C_6$-$C_{18}$-alkyl group or alkylene group. In one embodiment, when n is 1 and $R^2$ is mono-substituted, $R^2$ is a $C_1$-$C_{18}$-alkyl group or a $C_1$-$C_6$-alkyl-phenyl group. In one embodiment, $R^2$ is a $C_1$-$C_6$-alkyl group or a $C_1$-$C_3$-alkyl-phenyl group. In another embodiment, $R^2$ is a $C_1$-$C_3$-alkyl group or —$CH_2$-phenyl. In another embodiment, $R^3$ is H or $C_1$-$C_3$-alkyl, or H and —$CH_3$. In another embodiment, $R^4$ is $C_1$-$C_3$-alkyl, or —$CH_2$—$CH_3$ or —$CH_3$.

In one embodiment, the precursor compound of formula (IIIA) is

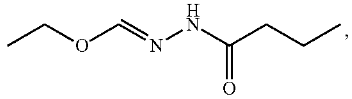

,

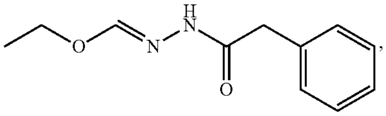

,

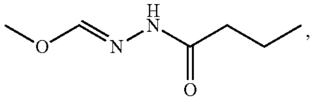

, or

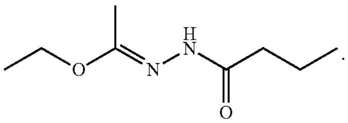

.

In one embodiment, when $R^2$ is a di-substituted $C_1$-$C_{18}$-hydrocarbyl radical, n is 2, and the precursor compound of formula (III) has the structure (IIIIB):

(IIIB)

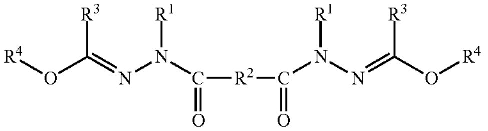

In one embodiment, when n is 2 and $R^2$ is mono-substituted, $R^2$ is a $C_6$-$C_{10}$-alkylene group. In one embodiment, when n is 2 and $R^2$ is mono-substituted, $R^2$ is a $C_1$-$C_{10}$-alkylene group or alkenylene group, or $R^2$ is a $C_4$-$C_{10}$-alkylene group or alkenylene group, or $R^2$ is a $C_6$-$C_{10}$-alkylene group or alkenylene group. In another embodiment, $R^3$ is H or $C_1$-$C_3$-alkyl, or H and —$CH_3$. In another embodiment, $R^4$ is $C_1$-$C_3$-alkyl, or —$CH_2$—$CH_3$ or —$CH_3$.

In another embodiment, the compound of formula (IIIB) is

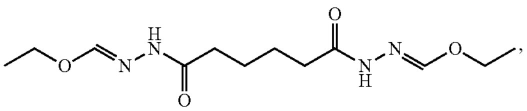

, or

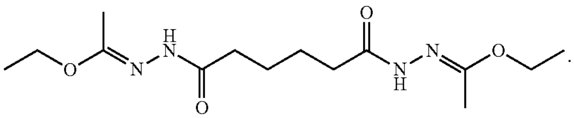

.

In one embodiment, when $R^2$ is a tri-substituted $C_1$-$C_{18}$-hydrocarbyl radical, n is 3, and the precursor compound of formula (III) has the structure (IIIC):

(IIIC)

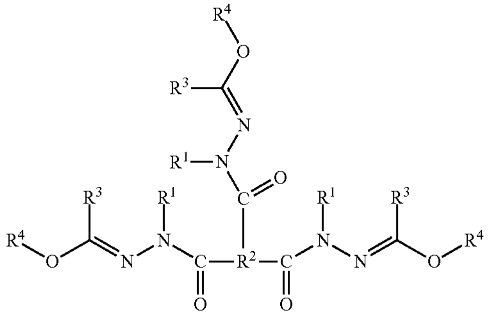

In one embodiment, when $R^2$ is a tetra-substituted $C_1$-$C_{18}$-hydrocarbyl radical, n is 4, and the precursor compound of formula (III) has the structure (IIID):

(IIID)

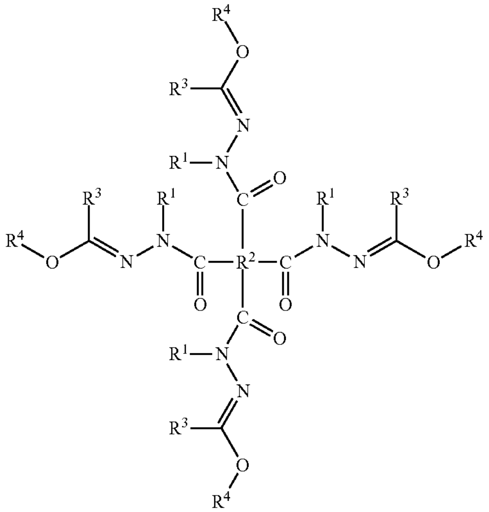

In another embodiment, $R^3$ is H or $CH_3$.

In another embodiment, $R^4$ is $C_1$-$C_5$-alkyl or phenyl. In another embodiment, $R^4$ is $C_1$-$C_5$-alkyl. In a further embodiment, $R^4$ is methyl or ethyl.

In another embodiment of the present disclosure, the precursor compounds are polymeric in which the hydrazide moiety is bound to polymeric backbones, such as polyethylene oxide or polysaccharide moieties. Accordingly, in one embodiment, there is included precursor compounds of the formula (IV):

(IV)

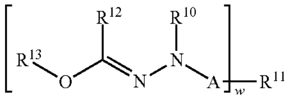

wherein

A is C═O, C═S, —S($O_2$)—, or —C═N—R', wherein R' is H or $C_1$-$C_5$-alkyl;

$R^{10}$ is H, $C_1$-$C_5$-alkyl, or phenyl;

$R^{11}$ represents a polyalkylene, polyol, polysaccharide, modified cellulose;

$R^{12}$ is H or $C_1$-$C_3$-alkyl;

$R^{13}$ is $C_1$-$C_5$-alkyl or $C_6$-$C_{10}$-aryl;

w is any integer from 2 to 5000.

In one embodiment, A is C═O.

In another embodiment, $R^{10}$ is H, $C_1$-$C_3$-alkyl, or phenyl. In another embodiment, $R^{10}$ is H, or $C_1$-$C_3$-alkyl. In another embodiment, $R^{10}$ is H.

In another embodiment, $R^{12}$ is H.

In another embodiment, $R^{13}$ is $C_1$-$C_5$-alkyl or phenyl. In another embodiment, $R^{13}$ is $C_1$-$C_5$-alkyl. In a further embodiment, $R^{13}$ is methyl or ethyl.

In another embodiment of the disclosure, upon being exposed to hydrolytic conditions, the precursor compounds of the formula (IV) release ester compounds of the formula (V)

(V)

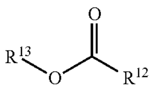

wherein $R^3$ is H or $C_1$-$C_3$-alkyl; and $R^4$ is $C_1$-$C_5$-alkyl or $C_6$-$C_{10}$-aryl.

In another embodiment, the ester compound of the formula (V) is ethyl formate:

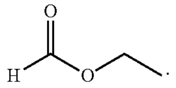

(III) Process to Prepare Precursor Compounds of the Disclosure

The present disclosure also includes a process for the preparation of the precursor compounds of the disclosure, including the precursor compounds of the formula (I), (III) and (IV). In one embodiment, the process comprises reacting the hydrazide moiety with an ortho-ester compound.

In one embodiment, the process for the preparation of the precursor compounds comprises the following reaction

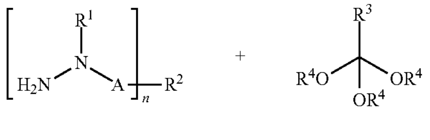

to provide a compound of the Formula (I)

(I)

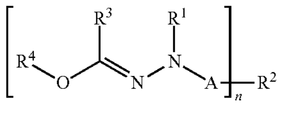

A is C═O, C═S, —S($O_2$)—, or —C═N—R, wherein R is H or $C_1$-$C_5$-alkyl;

$R^1$ is H, $C_1$-$C_5$-alkyl, or phenyl;

$R^2$ is a mono-, di-, tri- or tetra $C_1$-$C_{18}$-hydrocarbyl radical which is linear, branched or cyclic;

$R^3$ is H or $C_1$-$C_3$-alkyl;

$R^4$ is $C_1$-$C_5$-alkyl or $C_6$-$C_{10}$-aryl;

n is the integer 1, 2, 3, or 4.

In one embodiment, the reaction proceeds by reacting the hydrazide compound with an ortho-ester compound in a solvent such as ethanol and refluxed. In another embodiment, the reaction is performed neat.

In another embodiment, the process for preparing polymeric compounds of the formula (IV) is performed similarly and comprises the following reaction

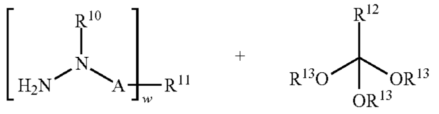

to provide a compound of the Formula (IV)

(IV)

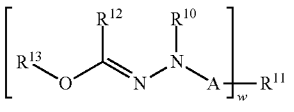

A is C═O, C═S, —S($O_2$)—, or —C═N—R', wherein R' is H or $C_1$-$C_5$-alkyl;

$R^{10}$ is H, $C_1$-$C_5$-alkyl, or phenyl;

$R^{11}$ represents a polyalkylene, polyethyleneglycol, polypropyleneglycol or a polysaccharide chain;

$R^{12}$ is H or $C_1$-$C_3$-alkyl;

$R^{13}$ is $C_1$-$C_5$-alkyl or $C_6$-$C_{10}$-aryl;

w is any integer from 2 to 5000.

(IV) Uses of the Precursor Compounds of the Disclosure

The precursor compounds of the present disclosure release ester compounds upon being exposed to hydrolytic conditions. Accordingly, in one embodiment of the disclosure, the identity and release, including the timing and rate of release, can be controlled by the selection of the precursor compound, and controlling the hydrolytic conditions. For example, in one embodiment, ester compounds such as propyl acetate, which has a fruity smell, can be released from the precursor compounds and the rate of release can be controlled by controlling the hydrolytic conditions. In one embodiment, the precursor compounds are useful for perfumery applications in which the release of the desired ester is controlled by the hydrolytic conditions for a long-lasting release of the ester.

In further embodiments, the ester EF can be released from the precursor compounds, and the EF released from the hydrolysis of the precursor compound can be used as a fumigant for killing pests and/or insects on fresh foods, such as fruits and vegetables. Accordingly, in one embodiment, the present disclosure includes a method for controlling, reducing or killing an infestation of pests on fresh food, such as fruits and vegetables, the method comprising subjecting the precursor compound of the formula (I) to hydrolytic conditions to release EF in the presence of the food, and wherein the EF prevents, controls, reduces or kills the infestation. In one embodiment, to release EF, $R^3$ is H and $R^4$ is ethyl. In another embodiment, by controlling the hydrolytic conditions, the rate of release of the EF can also be controlled. For example, a weak or mild organic acid, such as citric acid, can be used to hydrolyze the precursor compounds of the disclosure. In another embodiment, an acidic gas such as carbon dioxide can also be used to hydrolyze the precursor compounds. In one embodiment for example, the precursor compounds of the disclosure can be used for batch fumigation for controlling, reducing or killing an infestation of pests on fresh food by exposing the precursor to the acid, and the release of EF controls the infestation.

In other embodiments, the present disclosure also includes encapsulating the precursor compounds of formula (I) into carriers, such as film, nonwoven, coating, laminate structures suitable for the packaging of fresh foods, wherein, upon contact with an acid, the encapsulated precursor compound of formula (I) releases EF within the package to prevent, control, reduce or kill an pest or insect infestation. In one embodiment, the precursor compounds of the disclosure are electrospun into non-woven fibers and are useful in active packaging wherein the packaging material can be controlled to release an ester compound, for example EF, at a desired time to control or prevent a pest infestation.

Although the disclosure has been described in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present disclosure.

EXAMPLES

The operation of the disclosure is illustrated by the following representative examples. As is apparent to those skilled in the art, many of the details of the examples may be changed while still practicing the disclosure described herein.

Materials and Methods

Materials

Triethyl orthoformate (reagent grade, 98%), trimethyl orthoformate (reagent grade, 99%), triethyl orthoacetate (reagent grade, 97%), adipic acid dihydrazide (98%), phenylacetic hydrazide (98%), ethyl formate (reagent grade, 97%), ethyl cellulose (viscosity 22 cP, 48% ethoxyl content), and poly(ethylene oxide) (100 kDa) were purchased from Sigma-Aldrich (Oakville, ON, Canada). Butyric acid hydrazide (95%), anhydrous citric acid, 2-propanol, sodium chloride, potassium nitrate, and magnesium nitrate were bought from Fisher Scientific (Ottawa, ON, Canada). Anhydrous ethanol was supplied by Commercial Alcohol (Brampton, ON, Canada).

Example 1—Synthesizing Ethyl Formate Precursor

To synthesize EF precursor, two methods were adopted: In method (A), a suspension of adipic acid dihydrazide (500 mg), excess of triethyl orthoformate (5 mL), and anhydrous ethanol (20 mL) in a 50 mL, round-bottom flask were heated under reflux at 80° C. with stirring in an oil bath for 6 h. The solution was then stored overnight at 4° C. to form precipitates. The suspension was filtered, washed, and the particles were air dried to yield the precursor product. The filtrate was vaporized by vacuum drying at 40° C. to give an additional amount of the product. In method (B), a suspension of adipic acid dihydrazide (500 mg) and triethyl orthoformate (20 mL) was prepared in a 50 mL round-bottom flask was reflux at 110° C., with stirring, in an oil bath for 30 h. After cooling to room temperature, the mixture was filtered, and the residue was air dried.

Fourier Transformed Infrared (FTIR) Analysis

Infrared spectra of triethyl orthoformate, adipic acid dihydrazide, and products (A and B) were analyzed using an FTIR spectrometer (IRPrestige21, Shimadzu Corp., Kyoto, Japan) equipped with an attenuated total reflection (ATR) accessory (Pike Tech, Madison, WI, USA). Each sample was mounted on the ATR diamond crystal, compressed, and scanned 40 times in the region from 600 to 4000 $cm^{-1}$ at a resolution of 4 $cm^{-1}$. FTIR spectra were analyzed using the IRsolution software (Shimadzu Corp., Kyoto, Japan).

Nuclear Magnetic Resonance (NMR) Spectroscopy

Solid-state $^{13}C$ NMR spectroscopy was utilized to determine the molecular structure of the synthesized precursor. All solid-state NMR experiments were conducted at 298 K using a Bruker 500 MHz spectrometer (Avance II WB, Bruker Corporation, Billerica, MA, USA), operating at 11.74 T ($^{13}C$ Larmor frequency of 125 MHz). Dry samples were packed into 4 mm zirconia rotors and spun at 7 kHz at the magic angle spinning (MAS). Standard cross-polarization pulse sequence with total suppression of sidebands (CPTOSS) from Bruker library was employed for the experiments. A $^{1}H$ 90° pulse length of 2.95 μs, a contact time of 2 ms, and a recycle delay of 7.2 s were used. A total of 1000 scans were collected and spectra were processed with 50 Hz line broadening. The analysis of each spectrum was performed using TopSpin™ Software (Version 3.5pl7, Bruker Corporation, Billerica, MA, USA).

Differential Scanning calorimeter (DSC)

The thermal properties of adipic acid dihydrazide and the precursors were studied using a DSC (Q2000, TA Instruments, New Castle, DE, USA). Nitrogen with a flow rate of 18 mL/min was used as the purging gas. About 1.5-3.5 mg of the samples were accurately weighted in DSC aluminum pans and hermetically sealed with lids. An empty sealed pan was used as a reference. Samples were equilibrated at 20° C., then heated to 250° C. at a heating rate of 15° C./min. Thermograms were analyzed using TA Universal Analysis Software (TA Instruments, New Castle, DE, USA).

Particle Size Analyzer

Particle size distribution of the precursor was determined with a dynamic light scattering (DLS) particle size analyzer (Nanotrac Flex-180° DLS; Microtrac Inc., Montgomeryville, PA, USA). Samples were diluted in 2-propanol at a concentration of 0.5 mg/mL. Measurements were conducted at room temperature and a refractive index of 1.37 and 1.50 for fluid and particles, respectively. The data acquisition and analysis were done by Microtrac Flex software (Version 11.1.0.4, Microtrac Inc., Montgomeryville, PA, USA).

Scanning Electron Microscopy (SEM)

The morphological characteristics were examined using SEM (Quanta FEG 250, FEI Company, Hillsboro, OR, USA), at an accelerating voltage of 10 kV. Measurements were conducted for both the particles and the dried dilution which was prepared by dispersing the dilution on a layer of aluminum foil and air drying. Samples were mounted on metal stubs using double-sided adhesive carbon tape and coated with 20 nm conductive layer of gold on its surface using a sputter coater (Desk V TSC, Denton Vacuum, Moorestown, NJ, USA). Image analysis software (Image Pro-Premier 9.2, Media Cybernetics Inc., Rockville, MD, USA) was used to analyze the micrographs.

Headspace Analysis

The cumulative release of EF from the precursor was determined using an automatic headspace analysis system (FIG. 1). The system comprising of an environmental chamber (MLR-350H, Sanyo Electric Co., Ltd. Japan), a gas chromatograph (GC 6890, Agilent Technologies Inc., Santa Clara, CA, USA) equipped with a flame ionization detector (FID), stream selection valves (EMTCA-CE, VICI Valco Inst., Houston, TX, USA), 1/16 stainless steel tubing, and a control board (SRI Instruments Inc., Las Vegas, Nev., USA). The capillary column used with the GC was Agilent J&W DB-624 (Agilent Technologies Inc., Santa Clara, CA, USA) with 30 m length, 0.53 mm I.D, and 3 μm film thickness. The temperature of the detector and the oven were 200° C. and 40° C., respectively. The flow rates of $N_2$, $H_2$, and $O_2$ were 30, 50, and 200 mL/min, respectively. The calibration curve was prepared by measuring standard headspace concentration of a known amount of EF. Chromatograms were analyzed using the Peak Simple software (393-32 bit, SRI Instruments, CA, USA). At any given sampling point, the total amount of EF released into the headspace ($M_t$, μL) was determined according to Eqs. 5 to 7 by the addition of the recorded amount ($M_r$, μL) and the accumulated loss ($M_l$, μL) of all the previous sampling points up to that point.

$$M_r = C_r V_r \quad \text{(Eq. 5)}$$

$$M_l = \sum_{i=1}^{r-1} (C_{r-i} V_e) \quad \text{(Eq. 6)}$$

$$M_t = M_r + M_l \quad \text{(Eq. 7)}$$

where $C_r$ is the recorded EF concentration at that point (μL/L), which calculated based on calibration constants. $V_r$ and $V_e$ represent the volume of the jar (L) and the volume of headspace gas extracted from the jar (L), respectively.

Ethyl Formate Release Studies

To activate the release of EF, two approaches were evaluated. In the first approach, 1-2 mg of the precursor was placed in a 10 mL, glass beaker inside a hermetically sealed 1 L, glass jar as shown in FIG. 1. The headspace gas was extracted through a septum attached to the jar lid at predetermined time intervals. EF release was triggered by distributing 1 mL of 0.1 N citric acid on the precursor particles using a pipette (Fisher Scientific, Ottawa, ON, Canada) just before closing the jar and attaching it to the sampling needle. The release of EF from the precursor was studied at 5, 15, and 25° C.

In the second study, the release of EF was evaluated using an acidified substrate which was prepared by impregnating 0.3 mL of 5% (w/v) citric acid/anhydrous ethanol solution into a 3×3 cm spun-bound polypropylene nonwoven, followed by drying it overnight at 40° C. The precursor (1-2 mg) was then spreaded on the top of the acidified nonwoven layer and exposed to the test relative humidity maintained in a hermetically 1 L glass jar using silica gel (0% RH) or saturated salt solutions (magnesium nitrate, 53% RH; sodium chloride, 75% RH; potassium nitrate, 94% RH) (FIG. 1) (ASTM Standard E104-02 2012; Greenspan, 1977). EF release, expressed in milligram of EF per milligram of precursor per litre of headspace air, was determined using the headspace analysis system described above.

Stability Study

The stability of the precursor was studied over a period of 30 days. The precursor was stored at 25° C. under 0, 60, and 100% RH. An environmental chamber (MLR-350H, Sanyo Electric Co., Ltd. Japan) was used to control the humidity levels and temperature. Samples from each condition were tested for EF release at 1, 15, and 30th day at 25° C. using 0.1 N citric acid solution as described above.

Data Analysis

Differences between treatments were analyzed on SAS® University Edition software package (SAS Institute Inc., Cary, NC, USA.), using PROC GLIMMIX with one-way ANOVA. The means were compared using Tukey's honest significance difference test. P-values <0.05 were considered statistically significant. All treatments were triplicated and results were expressed as the mean values±standard error.

The release kinetics of EF from its precursor were modeled using an empirical pseudo-first order reaction kinetic model:

$$\frac{c_e - c}{c_e - c_0} = e^{-kt} \quad \text{(Eq. 9)}$$

where $C_e$ is the concentration of EF in the headspace of the 1 L test jar at an infinite time; C is the EF released at time, t; $C_0$ is the EF initial concentration (which was equal to zero in our case); and k is the release rate constants. Non-linear regression analyses were conducted to fit the release data and determine the model parameters.

Results and Discussion

Ethyl Formate Precursor Formation

The EF precursor was synthesized through the condensation between adipic acid dihydrazide and triethyl orthoformate. Here, two molecules of triethyl orthoformate were activated via heating to eliminate the ethanol moiety, followed by the nucleophilic addition of the amino groups of adipic acid dihydrazide molecule to form one molecule of diethyl N,N'-adipoyldiformohydrazonate as shown below in Scheme 1.

Scheme 1

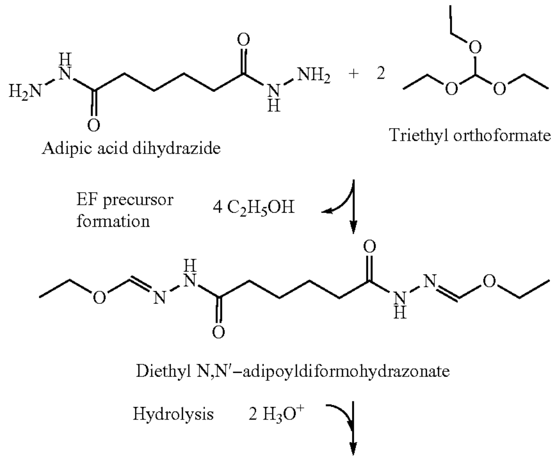

Adipic acid dihydrazide

Triethyl orthoformate

Diethyl N,N'-adipoyldiformohydrazonate

-continued

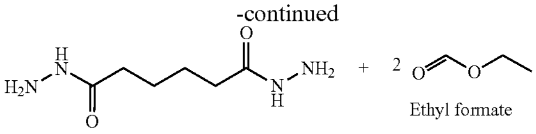

Adipic acid dihydrazide

Ethyl formate

Figure 2:
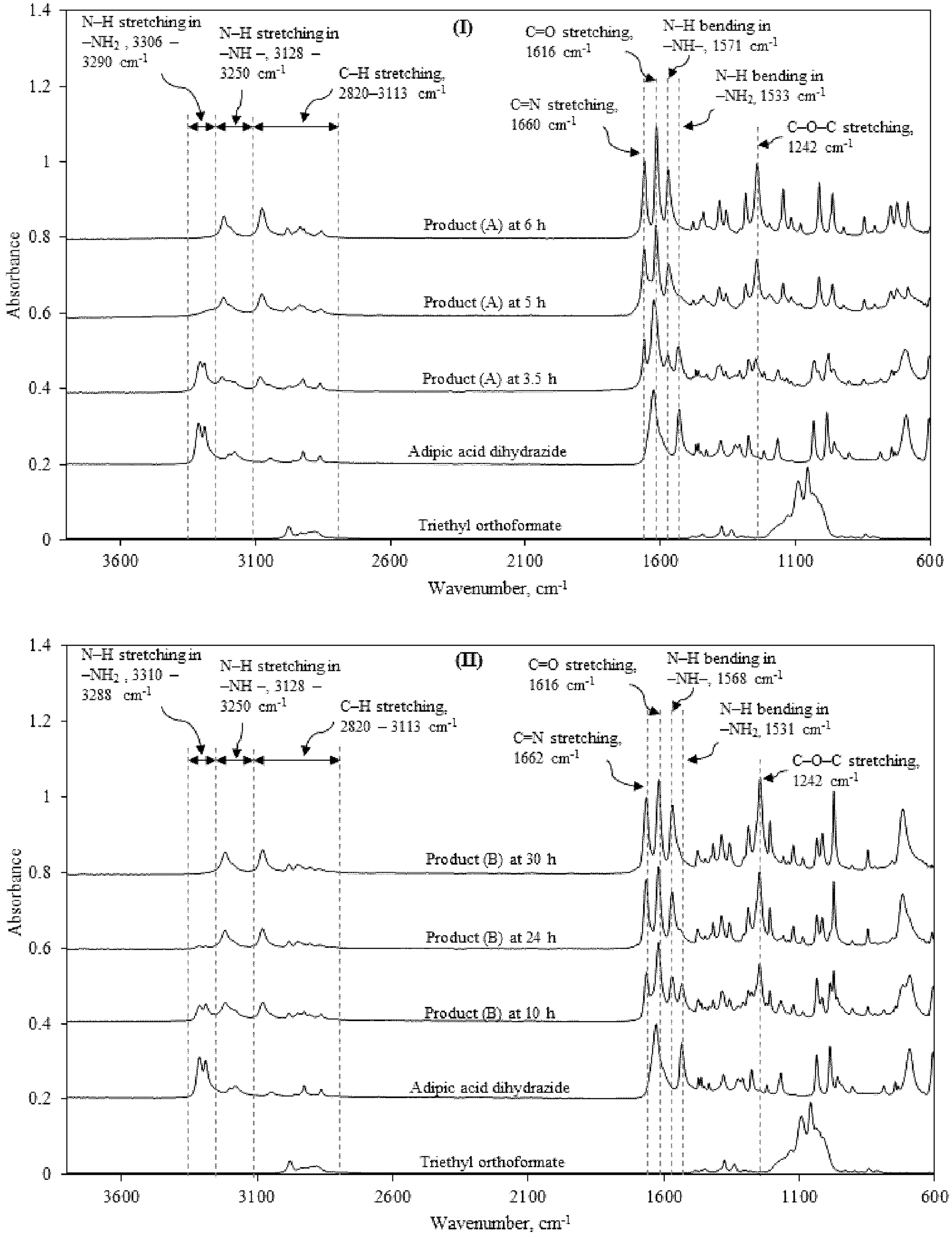
FIG. 2 is an Fourier transformed infrared (FTIR) spectra of a reaction mixture for the preparation of a precursor of the disclosure.

During the synthesis reaction with method (A), the initial white suspension turned into a colorless-clear solution after 3.5 h. The FTIR spectrum of the product at 3.5 h (FIG. 2(I)) showed that the reaction was incomplete, as shown by the existence of N—H stretching at 3306-3290 $cm^{-1}$ and N—H bending at 1533 $cm^{-1}$ of the —$NH_2$ moiety of the dihydrazide. The three absorbance at 1660, 1571, and 1242 $cm^{-1}$, which were absent for adipic acid dihydrazide and triethyl orthoformate spectra, could be attributed to C═N stretching, N—H bending in —NH—, and C—O—C stretching of the EF precursor, respectively. The intensity of these peaks increased as the reaction progressed to 5 h due to the further formation of the precursor. Moreover, at 5 h, the —$NH_2$ bands (stretching at 3306-3290 $cm^{-1}$ and bending at 1533 $cm^{-1}$) diminished, due to the further depletion of adipic acid dihydrazide substrate, although these bands were still noticeable on the spectrum, indicating that the substrate was not totally exhausted. Additionally, the absorbance signals at 750-630 $cm^{-1}$ could be related to out of plane N—H bending or $CH_2$ wagging. Out of plane C—H bending could be responsible for the peaks present at 962 $cm^{-1}$. Stretching vibration of C—N and C═O were found at 1013 and 1616 $cm^{-1}$, respectively. The peaks around 2820-3113, and 3128-3250 $cm^{-1}$ are related to C—H stretching in —$CH_2$—, —$CH_3$ and N—H stretching in —NH—, respectively (Günzler and Gremlich, 2002; Pavia, D., Lampman, G., Kriz, G., Vyvyan, 2013). At 6 h, the product showed further increased intensity of C═N stretching at 1660 $cm^{-1}$, —NH— bending at 1571 $cm^{-1}$, and C—O—C stretching at 1242 $cm^{-1}$ of the precursor and absence of —$NH_2$ bands of adipic acid dihydrazide. These observations indicate that the adipic acid dihydrazide substrate was depleted, and therefore, the reaction in method (A) was stopped at 6 h, giving ~94% yield of the product.

By contrast, in method (B), the white suspension persisted throughout the entire synthesis process. The FTIR spectra of the product (FIG. 2(II)) collected at 10 and 24 h showed the existence of adipic acid dihydrazide, as evidenced by the presence of —$NH_2$ absorbance bands (N—H stretching at 3310-3288 $cm^{-1}$ and N—H bending at 1531 $cm^{-1}$). The spectra also showed C═N stretching at 1662 $cm^{-1}$, —NH— bending at 1568 $cm^{-1}$, and C—O—C stretching at 1242 $cm^{-1}$ of the precursor, as in product (A) spectra, indicating the formatin of the precursor compound. Similar to the spectra from Method (A), the broad signal at 716 $cm^{-1}$ could be caused by out of plane N—H bending or $CH_2$ wagging. The high-intensity band at 970 $cm^{-1}$ which could be related to out of plane C—H bending. Stretching signals of C—N could be responsible for the peaks at 1013-1033 $cm^{-1}$. The peaks at 1616, 2820-3113, and 3128-3250 $cm^{-1}$ could be corresponding to the stretching vibration of C═O, C—H, and —NH—, respectively (Günzler and Gremlich, 2002; Pavia, D., Lampman, G., Kriz, G., Vyvyan, 2013). At 30 h, the intensity of the characteristic bands of the precursors, i.e., C═N stretching (1662 $cm^{-1}$), —NH— bending (1568 $cm^{-1}$), and C—O—C stretching (1242 $cm^{-1}$) increased further, with concomitant disappearance of the —$NH_2$ bands, suggesting the completion of the reaction. Therefore, the reaction in method (B) was stopped at 30 h and the white particles were collected to give ~91% yield.

Figure 3:
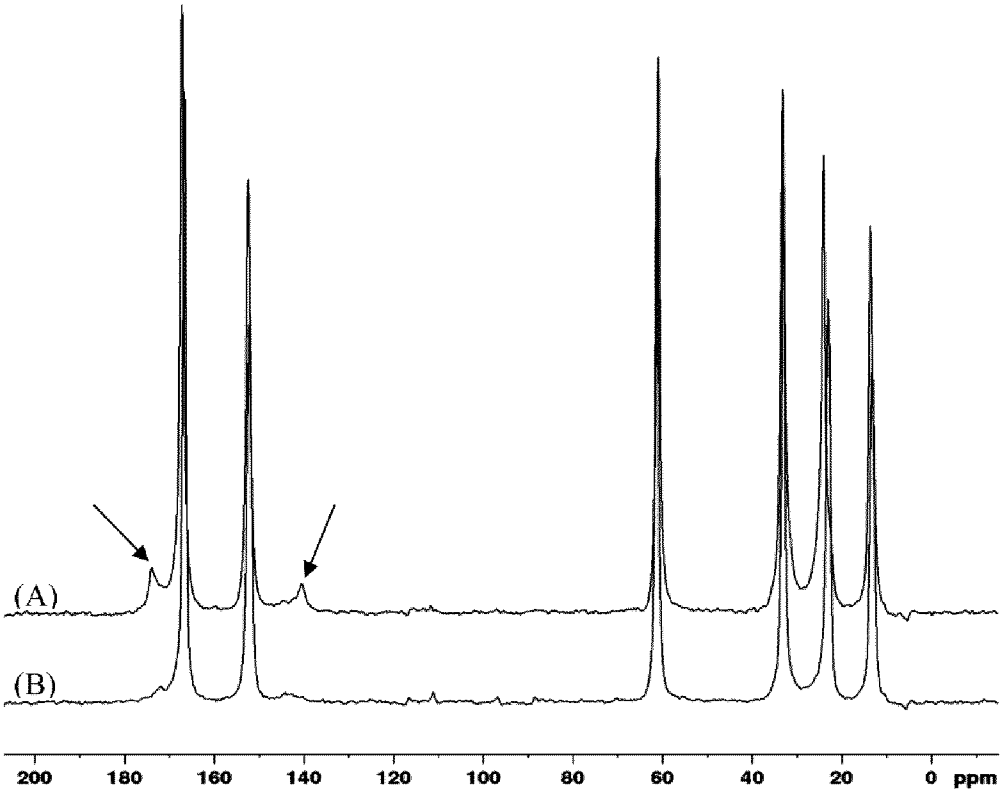
FIG. 3 is a Solid-state $^{13}C$ nuclear magnetic resonance (NMR) spectra for a precursor of the disclosure.

Solid-state $^{13}C$ NMR spectroscopy was used to confirm the molecular structure of the synthesized precursor. The NMR analysis confirmed the structure of products (A and B) to be diethyl N,N'-adipoyldiformohydrazonate structure (FIG. 3): $^{13}C$ NMR (500 MHZ, δ in ppm): δ=167 (—C═O); 152 (HC═N—N); 61 ($H_2C$—O—CH); 33 ($H_2C$—C═O); 23 ($H_2C$—$CH_2$—$CH_2$); 13 ($H_2C$—$CH_3$). As shown from the NMR analysis, precursor spectra from Method (A) exhibited additional peaks at 140 and 174 ppm that were absent from that derived from Method (B). The origins of the these two peaks are unclear, although they are indicative of other presence of other chemical species, possibly, 4-di(1,3,4-oxadiazol-2-yl)butane.

Thermal Analysis

Figure 4:
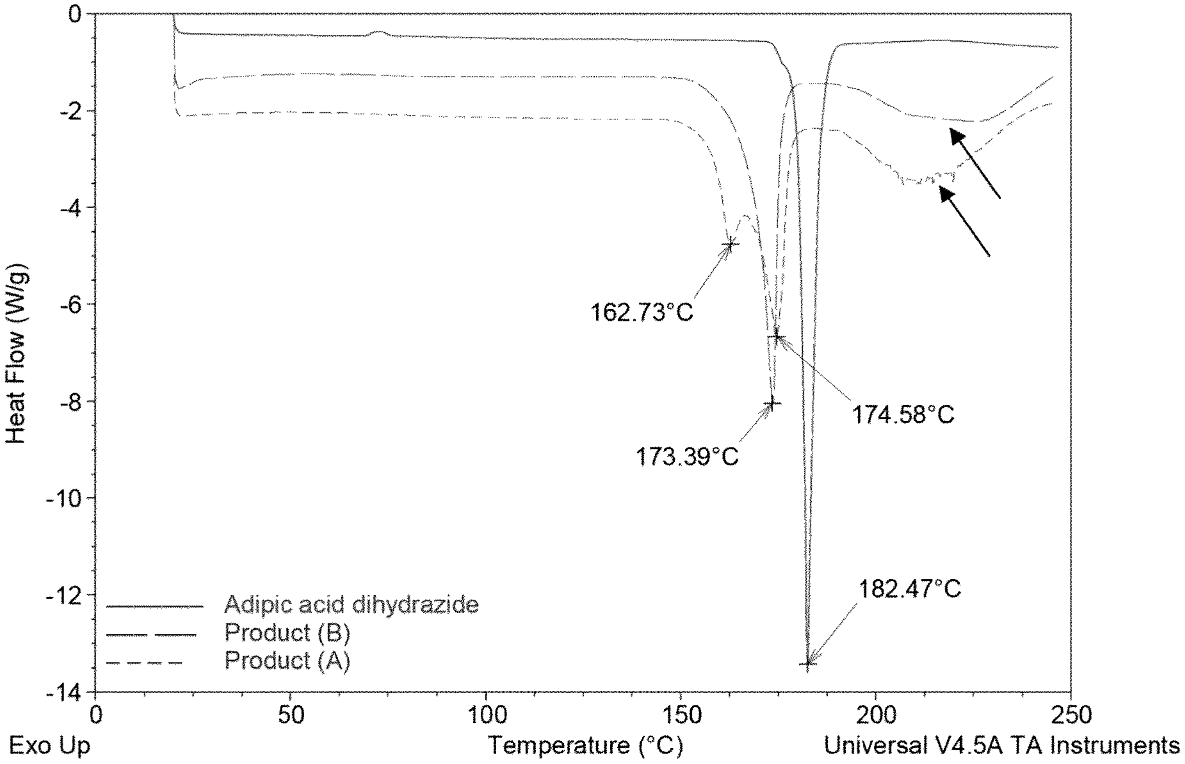
FIG. 4 is a differential scanning calorimetry (DSC) thermogram showing the decomposition of a precursor of the disclosure.
Figure 5:
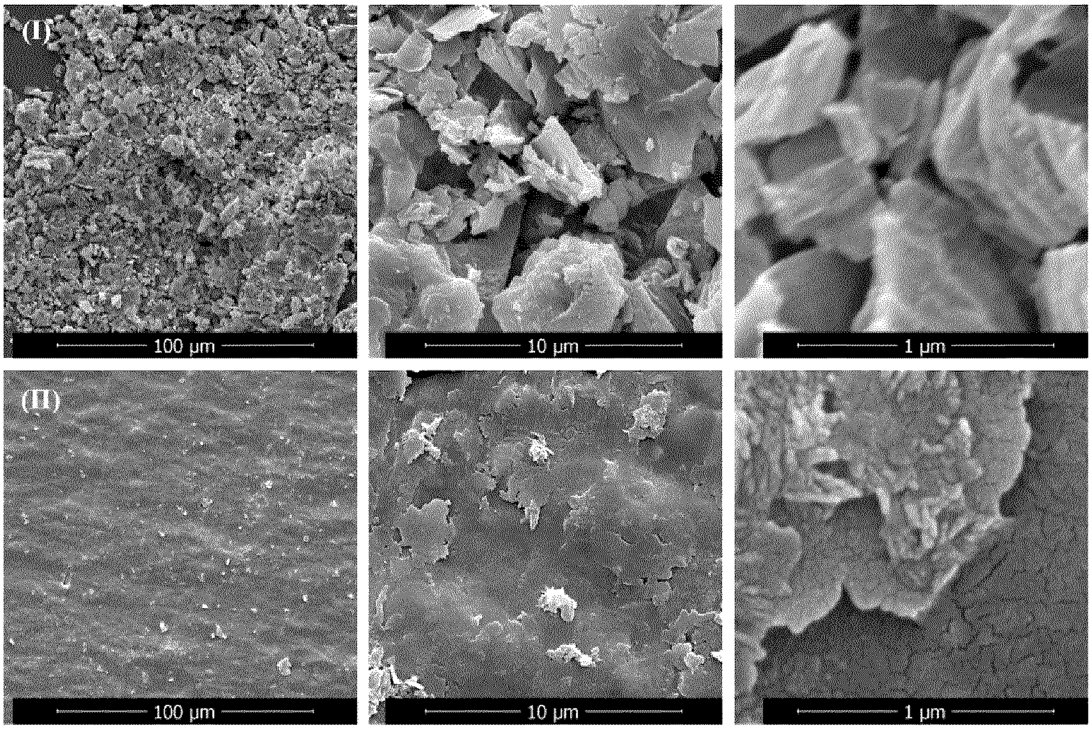
FIG. 5 are scanning electron microscope (SEM) micrographs of a precursor of the disclosure.

In accordance with the FTIR and NMR results presented above, the DSC thermogram of the precursor from Method (A) showed a small shoulder at 164.6±0.9° C. before the maximum peak at 174.9±1.1° C. (FIG. 5). The two overlapped endothermic peaks suggested the melting points of two compounds in a physical mixture. The first peak was likely due to the impurity, while the larger peak the precursor. On the other hand, precursor from method (B) showed only one melting peak with a melting temperature of 173.9±0.9° C., which was not significantly different ($P>0.05$) from that from method (A). Moreover, the enthalpies of melting were 207.9±7.3 and 204.7±3.5 J/g for methods (A) and (B), respectively, suggesting that the presence of the impurity did not affect the melting properties of the precursor. Both precursors from methods (A) and (B) started to decompose above the melting point, at around 194° C., which could be related to the decomposition of —C═N— and C—O—C which have medium to low decomposition energy (Grewer, 1991). The perturbation of the thermograms at the decomposition regions (arrows in FIG. 4) can be attributed to the volatilization of gases from the decomposed samples. Similar behavior was reported by Mathkar et al., (2009) for pharmaceutical compounds (azatadine maleate and labetalol hydrochloride). The thermal decomposition region was not observed in the thermogram for adipic acid dihydrazide, which only showed a sharp melting peak at 182.5° C. indicating its thermal stability within the temperature range investigated.

Particle Size Distribution and Morphology

Figure 6:
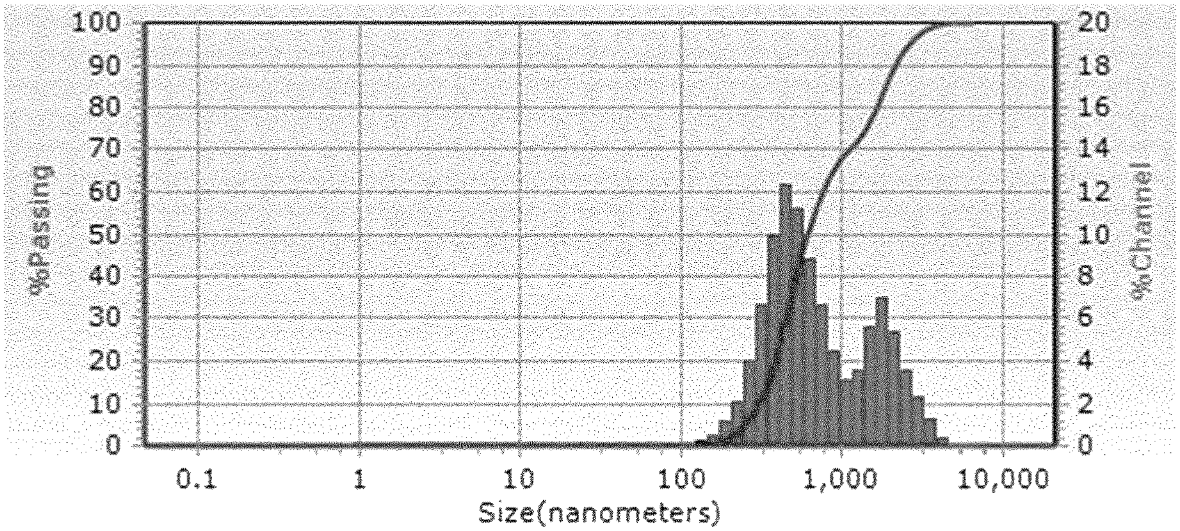
FIG. 6 shows the particle size distribution of a precursor of the disclosure.

The SEM micrographs showed that the precursor from method (B) was made up of agglomerated particulates with irregular shapes and sizes (FIG. 5(I)). In preliminary studies, attempts were done to disperse the precursor particulates in water; however, the agglomerates presisted even after 5 h of stirring, indicating that the hydrophobicity of the precursor. However, the particulates could be dispersed in 2-propanol to form a milky suspension. The size distribution of the particles was measured using DLS. As shown in FIG. 6, relatively wide size distribution (range of 145-4620 nm) was observed containing two diameter peaks at 467 and 1796 nm with volume percentage (passing) of 67.8 and 32.2%, respectively. The microstructure of the particles from the dried dilution proved that the chunks were dispersed into fine particles and formed a continuous layer (FIG. 5(II)) at low magnification, although small aggregates were visible in the micrograph, especially at higher magnifications.

Example 2—Activated Release of Ethyl Formate

Figure 7:
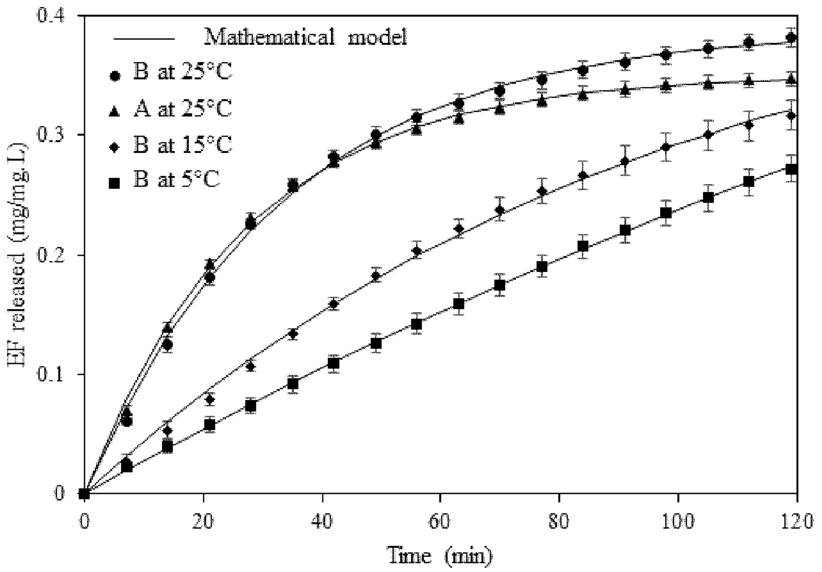
FIG. 7 is a graph showing the amount of ester compound released from a precursor compound of formula (I) subjected to hydrolytic conditions. The unit "mg/mg·L" is referring to milligram of EF per milligram of precursor per litre of headspace air.

The release of EF vapor was achieved through the hydrolysis of the C═N on diethyl N,N'-adipoyldiformohydrazonate, as illustrated in Scheme 1. In the first study, the release was activated using 0.1 N citric acid solution at 5, 15, and 25° C. to simulate different storage temperatures for fruits and vegetables. As shown in FIG. 7, increasing the temperature significantly ($p<0.05$) increased the release rate of EF. At 25° C., rapid releases were observed for precursors from both methods within the first 60 min, followed by slower release profiles. The accumulative EF releases of precursors from methods (A) and (B), after 120 min, were not significantly different ($P>0.05$), at 0.35±0.006 and 0.38±0.002 mg/mg·L, respectively (see Table 1). At 15 and 5° C., slower release trends were observed with accumulative releases of 0.32±0.013 and 0.26±0.011 mg/mg·L, respectively, at 120 min. Similar behaviors were reported by Jash and Lim (2018) on activated release of hexanal from its imidazolidine precursor, as temperature increased from 5 to 45° C.

The release data were fitted satisfactory using the pseudo-first-order kinetic model (Eq. 9) with $R^2$ around 0.99 (see Table 1). The release rate constant (k) increased significantly ($p<0.05$) with increasing temperature. Moreover, differences in $C_e$ values were not significant ($P>0.05$) between precursors prepared from the two methods.

Figure 8:
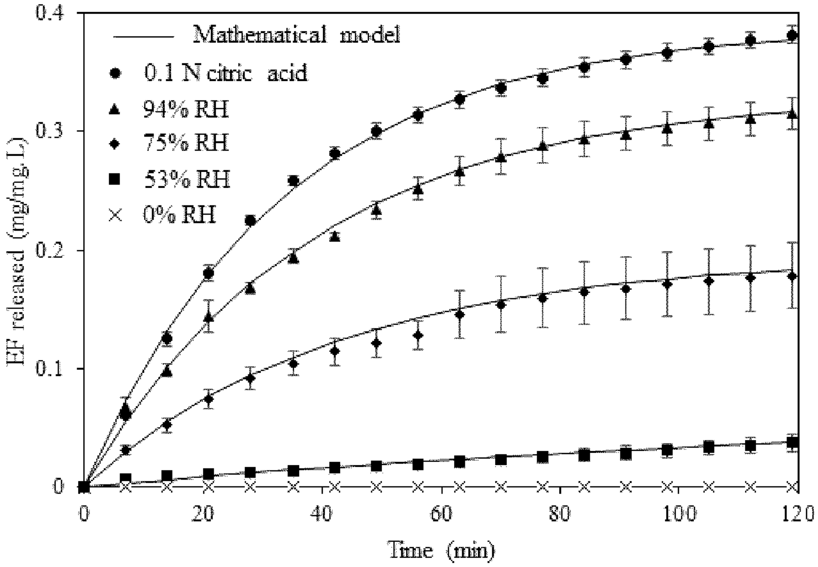
FIG. 8 is a graph showing the amount of ester compound released from a precursor compound of formula (I) subjected to different hydrolytic conditions. The unit "mg/mg·L" is referring to milligram of EF per milligram of precursor per litre of headspace air.

In the second study, the release of EF from its precursor, prepared using method (B), was activated using an acid-dispersed substrate at 25° C. under 0, 53, 75, and 94% RH conditions. The activation first involved the absorption of moisture in headspace by the citric acid impregnated in the nonwoven substrate, to form citric acid solution. The acidic solution came in contact with the precursor dispersed on the top of the nonwoven substrate, thereby catalyzed the hydrolysis of the precursor, triggering the release of EF vapor. Accordingly, increasing RH in the headspace significantly enhanced EF release rate (FIG. 8). At 94% RH, the release achieved at 120 min was 0.32±0.014 mg/mg·L (80.8% release), while at 75% RH, the amount of EF released was significantly ($p<0.05$) reduced by half (see Table 2). In contrast, at 53% RH, only 9.6% of the release was obtained and no release was observed at 0% RH. A pseudo-first order kinetic equation (Eq. 9) was fitted to the release data. The estimated parameters are summarized in Table 2. As shown, the k value increased significant as RH increased from 0 to 75% RH, although the difference in k value was not significant ($p>0.05$) between 75 and 74% RH. Similarly, $C_0$ increased significantly ($p<0.05$) with increasing RH. This RH-dependent release behaviour can be beneficial during end-use applications. For example, in active packaging, an increase in RH of package headspace can be used as an activator to trigger the release of EF from the precursor, such as packages for fruits and vegetables (Lee et al., 1995; Petersen et al., 1999; Ragaert, Devlieghere, and Debevere, 2007).

Stability of Precursor

Figure 9:
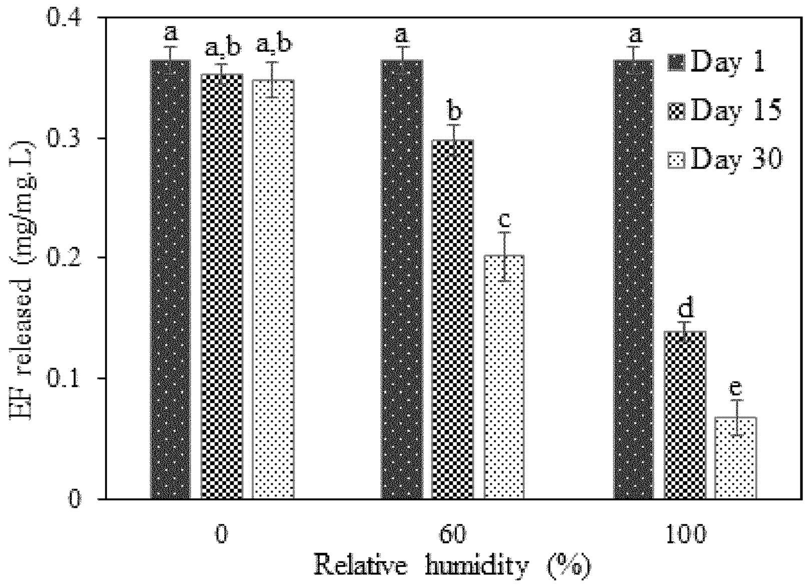
FIG. 9 is a graph showing the storage stability of a precursor of the disclosure at different relative humidity conditions. The unit "mg/mg·L" is referring to milligram of EF per milligram of precursor per litre of headspace air.

To evaluate the storage stability of the EF precursor, it was evaluated for up to 30 days at 25° C. under 0, 60, and 100% RH conditions. The precursor showed high stability at 0% RH, where no significant ($p>0.05$) changes were detected in the amount of EF released for days 1, 15, and 30 (see FIG. 9). However, there was an 18 and 45% reduction in EF release from the samples stored at 60% RH after 15 and 30 days, respectively. At 100% RH, the extents of reduction increased to 62 and 81% for 15 and 30 days, respectively. The decreased stability of the precursor with increasing RH can be attributed to the auto-hydrolysis of the precursor during prolonger storage, which can be effective arrested by storing the precursor under 0% RH environment to maximize the availability of EF.

Example 3—Encapsulation of Precursor in Electrospun Fibers

Figure 10:
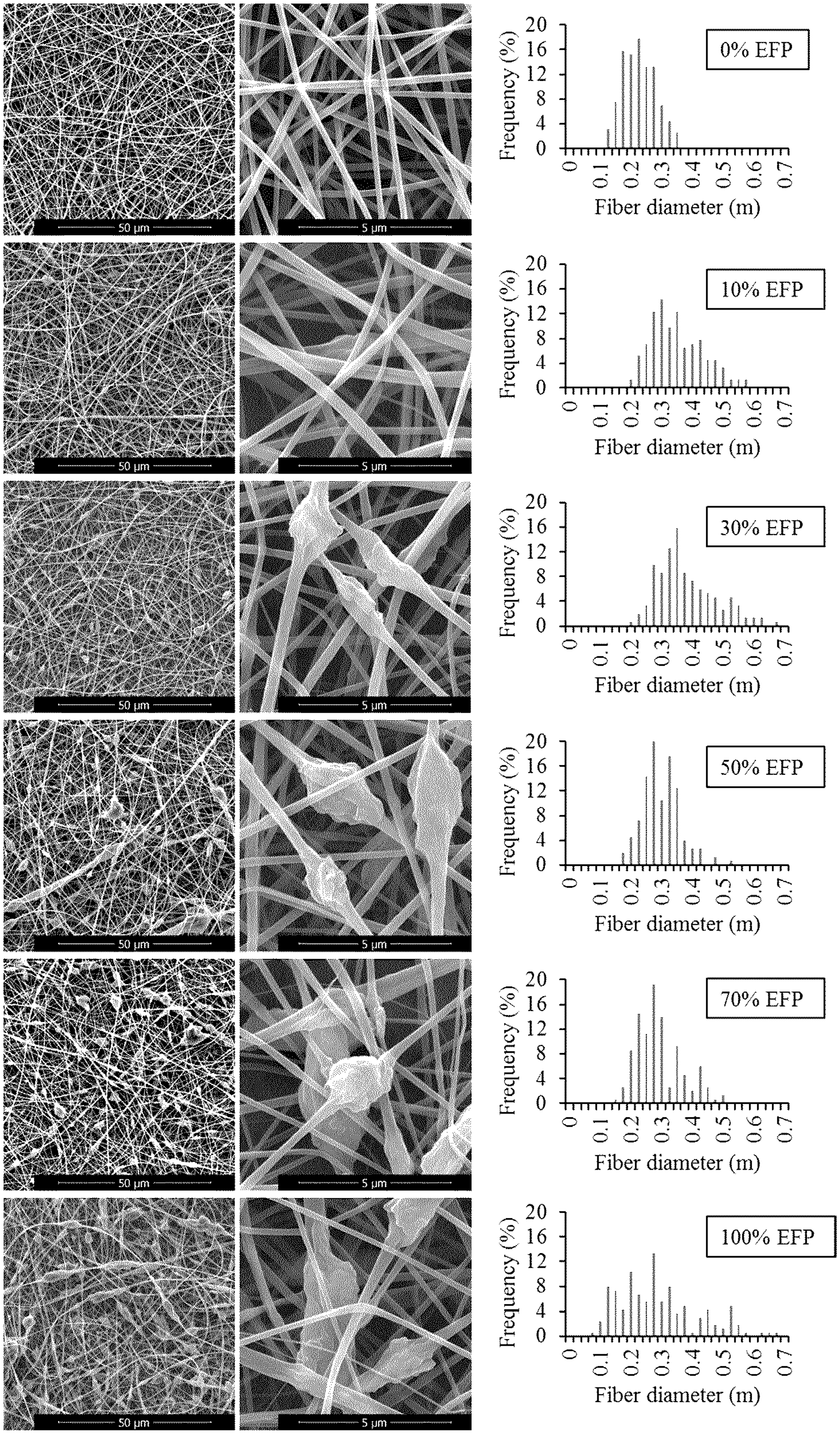
FIG. 10 are SEM micrographs and histograms of fibers diameter distribution of EC-PEO nonwovens loaded with an EF precursor (EFP) at 0, 10, 30, 50, 70, and 100% (w/w, polymer basis).

The EF precursor from Example 1 was encapsulated in electrospun fibers using a free surface electrospinner. A spin dope solution of 10% (w/w) ethyl cellulose (EC) and 1% (w/w) poly(ethylene oxide) (PEO) in 90% (v/v) aqueous ethanol was prepared, to which EF precursor at 10, 30, 50, 70, 100% (w/w; polymer content basis) was added. About 5-10 g of the solution was loaded into the carriage and electrospun at a carriage speed of 100 mm/s and a voltage of 40 kV. The morphological structures of pristine and precursor-loaded EC-PEO electrospun nonwovens, along with their diameter distribution, are shown in FIG. 10. The SEM micrographs show that neat EC-PEO nonwoven (0% EF precursor) had continuous bead-free fibers with cylindrical-like morphology and an average fiber diameter of 0.215±0.053 μm. The incorporation of EF precursor did not affect the morphology of the fibers. However, irregular entities, which were larger in size than the diameter of the fibers, were observed. On the basis that the count of the irregular entities increased with increasing EF precursor content, these entities were the EF precursor particles encapsulated within the fiber polymer matrix, having particle size distribution ranging from 0.145 to 4.620 μm. At low magnifications, it can be seen that the EF precursor particles were dispersed uniformly throughout the nonwovens. These results suggested that EC-PEO nonwovens can be a promising a carrier for entrapping EF precursor particles.

Example 4—Ethyl Formate Release from Electrospun Nonwovens

Figure 11:
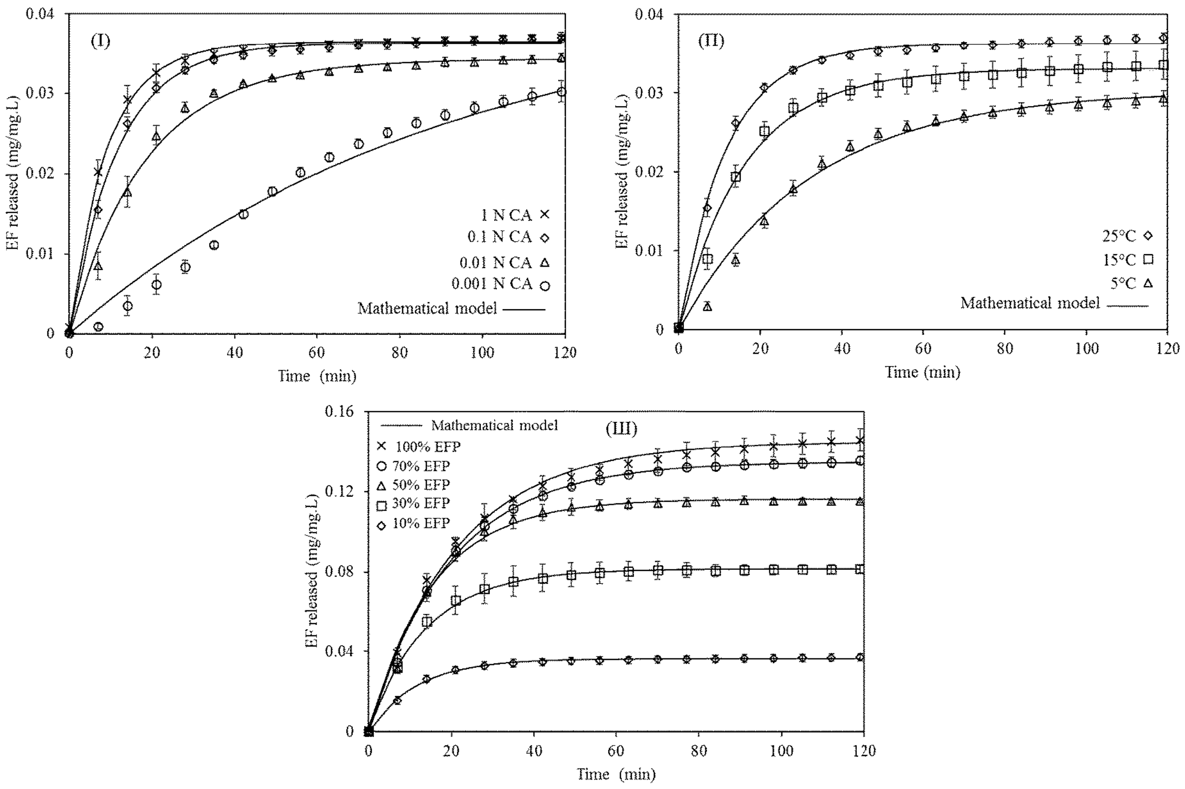
FIG. 11 are graphs showing the release of EF from a precursor embedded in EC-PEO electrospun fibers as affected by the concentration of CA solution (I), temperature (II), and EF precursor (EFP) loading capacity (III). EF release was expressed in mg/mg·L (milligram of EF vapor per milligram of nonwoven per liter of headspace air).

The release of EF from the 10, 30, 50, 70, and 100% EF precursor-loaded nonwovens in Example 3 was triggered by distributing citric acid (CA) solutions of different concentrations (0.001, 0.01, 0.1, and 1 N) on the surface of the precursor-loaded nonwovens. The release of EF was studied at 5, 15, and 25° C. using gas chromatography. The release data were modeled by the pseudo-first-order kinetic equation (Eq. 9), with $R^2$ values above 0.98. The resulting parameters (Ce and k) for the fitted model are presented in Table 3. As shown in FIGS. 11(I) and 11(II), increasing CA concentration and temperature significantly ($p<0.05$) increased the release rate of EF vapor from the nonwovens. Expectedly, increasing EF precursor loading from 10 to 100% (w/w; polymer content basis) increased the accumulated EF released [FIG. 11(III)]. Comparing the release profiles of EF from the precursor-loaded nonwovens with those from the precursor particles, the former showed faster release rate due to larger surface area-to-volume ratio of the electrospun fibers than that of the EF precursor particles. This result illustrated the release rate enhancement effect of electrospun fibers on the EF precursor.

Example 5—Preparation of ethyl N-butyrylformohydrazonate

Scheme 2

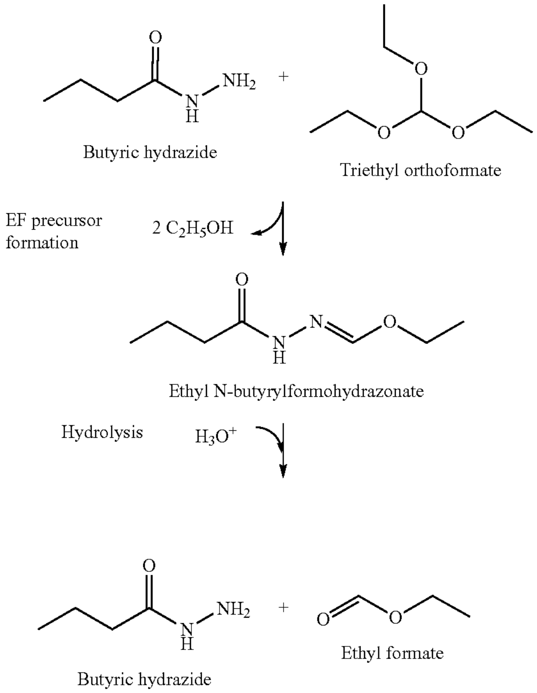

Butyric hydrazide
Triethyl orthoformate
Ethyl N-butyrylformohydrazonate
Butyric hydrazide
Ethyl formate Butyric hydrazide (1000 mg), excess triethyl orthoformate (5 mL), and anhydrous ethanol (20 mL) were mixed in a 50 mL round-bottom flask to form a homogeneous solution, followed by heating under reflux at 85° C. with stirring in an oil bath for 7 h. The solution was vacuum dried at 40° C. to yield the EF precursor powder product—ethyl N-butyrylformohydrazonate (Scheme 2). $^{13}C$ NMR (600 MHZ, δ in ppm): δ=168.3 (—C═); 155.1 (HC═N—N); 62.6 ($H_2C$—O—CH); 36.5 ($H_2C$—C═O); 18.1 ($H_2C$—$CH_2$—$CH_3$); 15.7 (—O—$H_2C$—$CH_3$); 14.1 ($H_2C$—$H_2C$—$CH_3$). The EF precursor can be hydrolyzed under mild acidic conditions to trigger the release of EF.

Example 6: Preparation of ethyl N-(2-phenylacetyl)formohydrazonate

Scheme 3

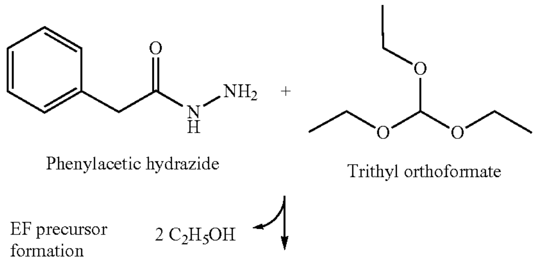

Phenylacetic hydrazide
Trithyl orthoformate

-continued

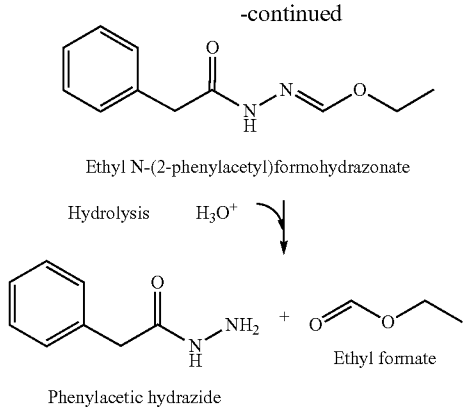

Ethyl N-(2-phenylacetyl)formohydrazonate
Phenylacetic hydrazide
Ethyl formate

Phenylacetic hydrazide (500 mg), excess of triethyl orthoformate (2 mL), and anhydrous ethanol (15 mL) were mixed in a 50 mL round-bottom flask to form a homogeneous solution, followed by heating under reflux at 85° C. with stirring in an oil bath for 7 h. The solution was vacuum dried at 40° C. to yield the EF precursor powder product—ethyl N-(2-phenylacetyl)formohydrazonate (Scheme 3). $^{13}C$ NMR (600 MHZ, δ in ppm): δ=171.3 (—C═O); 155.5 (HC═N—N); 136.5 (Ph C(1')); 129.7 (Ph C(2') or Ph C(3')); 129.4 (Ph C(2') or Ph C(3')); 126.7 (Ph C(4')); 62.9 ($H_2C$—O—CH); 41.6 ($H_2C$—C═O); 14.6 ($H_2C$—$CH_3$). The EF precursor can be hydrolyzed under mild acidic conditions to trigger the release of EF vapor.

Example 7: Preparation of Methyl N-butyrylformohydrazonate

Scheme 4

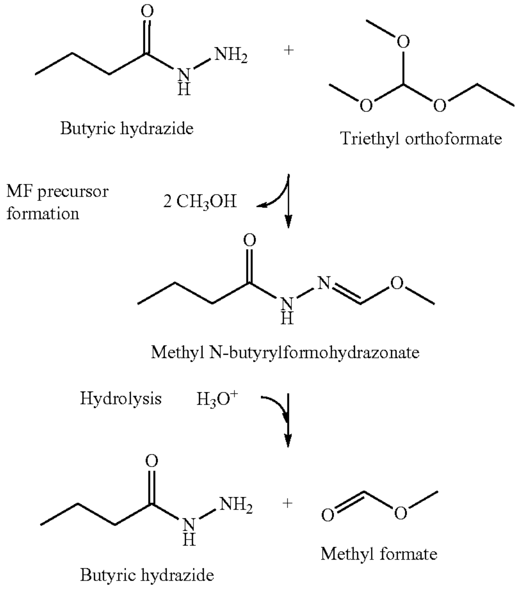

Butyric hydrazide
Triethyl orthoformate
Methyl N-butyrylformohydrazonate
Butyric hydrazide
Methyl formate Butyric hydrazide (1000 mg), excess of trimethyl orthoformate (3 mL), and anhydrous ethanol (20 mL) were mixed in a 50 mL round-bottom flask to form a homogeneous solution, followed by heating under reflux at 85° C. with stirring in an oil bath for 7 h. The solution was vacuum dried at 40° C. to yield the methyl formate (MF) precursor powder product—methyl N-butyrylformohydrazonate (Scheme 4). $^{13}C$ NMR (600 MHZ, δ in ppm): δ=168.3 (—C═O); 155.0 (HC═N—N); 54.2 (—O—$CH_3$); 36.7 ($H_2C$—C═O); 19.0 ($H_2C$—$CH_3$); 14.3 ($H_2C$—$CH_3$). The MF precursor can be hydrolyzed under mild acidic conditions to trigger the release of MF.

Example 8: Preparation of Diethyl N,N'-adipoyldiacetohydrazonate

Scheme 5

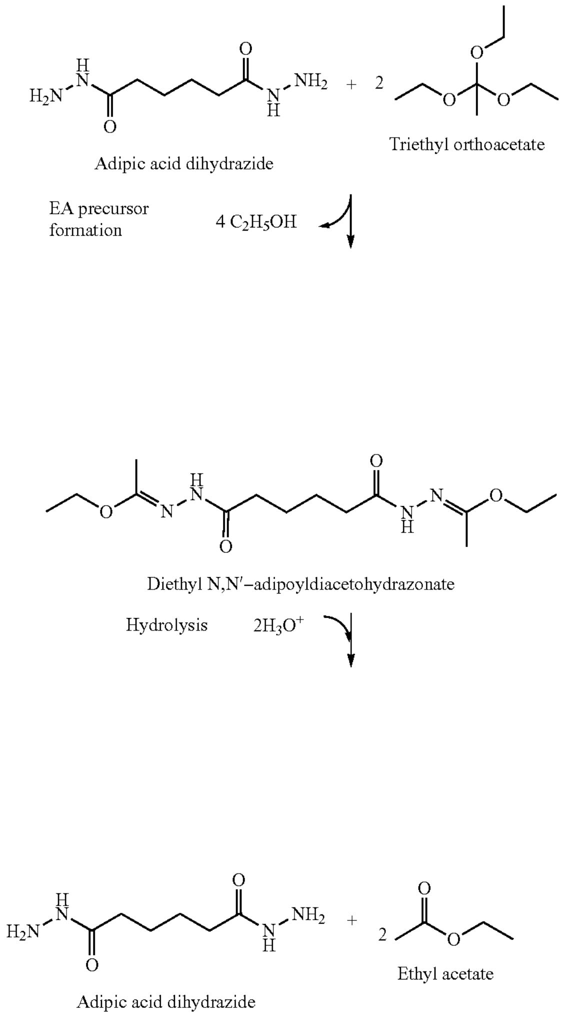

Adipic acid dihydrazide (300 mg), excess of triethyl orthoformate (3 mL), and anhydrous ethanol (20 mL) in a 50 mL round-bottom flask to form a suspension, followed by heating under reflux at 80° C. with stirring in an oil bath for 6 h. The solution was vacuum dried at 40° C. to yield the ethyl acetate (EA) precursor powder product—diethyl N,N'-adipoyldiacetohydrazonate (Scheme 5). $^{13}C$ NMR (600 MHZ, δ in ppm): δ=167.9 (—C═O); 164.5 ($H_3C$—C═N); 62.1 ($H_2C$—O—C); 34.3 ($H_2C$—C═O); 24.4 ($H_2C$—$CH_2$—$CH_2$); 15.7 ($H_2C$—$CH_3$); 14.6 (C—$CH_3$). The EA precursor can be hydrolyzed under mild acidic conditions to trigger the release of EA vapor.

Example 9: Preparation of ethyl N-butyrylacetohydrazonate

Scheme 6

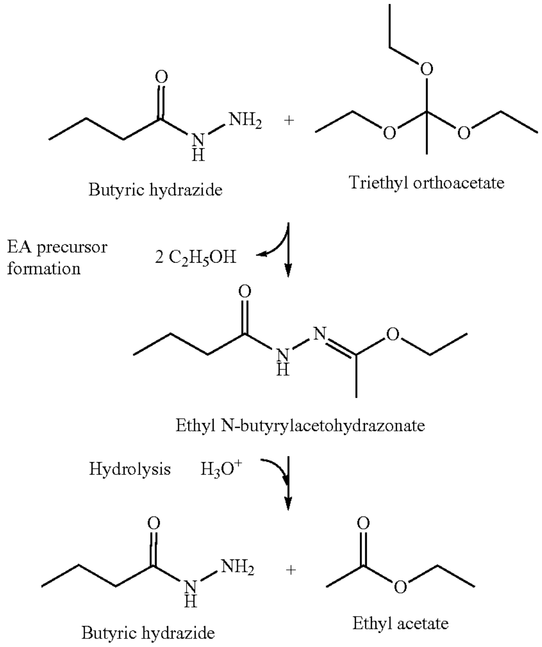

Butyric hydrazide (1000 mg), excess of triethyl orthoacetate (3 mL), and anhydrous ethanol (20 mL) in a 50 mL round-bottom flask to form a homogeneous solution, followed by heating under reflux at 85° C. with stirring in an oil bath for 7 h. The solution was vacuum dried at 40° C. to yield the EA precursor powder product—ethyl N-butyrylacetohydrazonate (Scheme 6). $^{13}C$ NMR (600 MHZ, δ in ppm): δ=168.0 (—C═O); 164.4 (C═N); 62.0 ($H_2C$—O—C); 36.4 ($H_2C$—C═O); 18.9 ($H_2C$—$CH_2$—$CH_3$); 15.7 (—O—$H_2C$—$CH_3$); 14.5 ($H_2C$—$H_2C$—$CH_3$); 13.8 (C—$CH_3$). The EA precursor can be hydrolyzed under mild acidic conditions to trigger the release of EA vapor.

Figure 12:
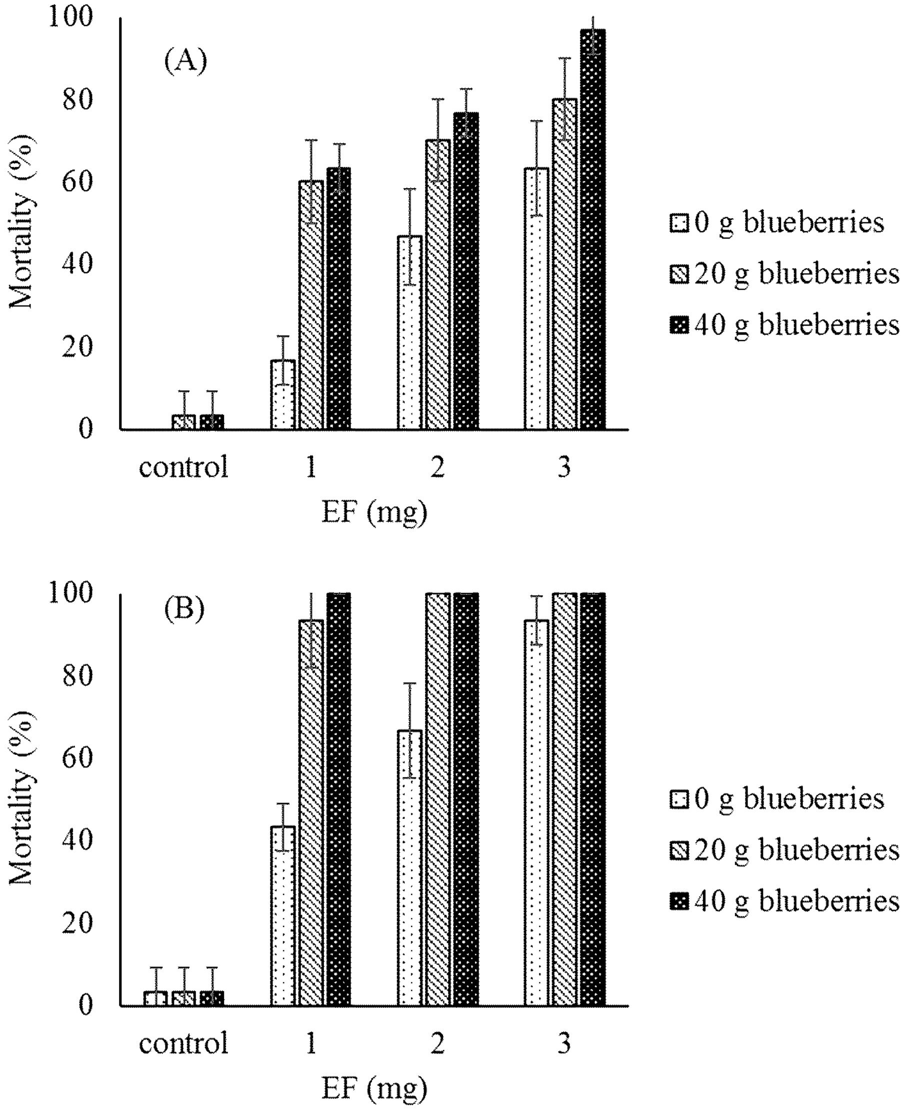
FIG. 12 are graphs showing the mortality of spotted-wing *Drosophila* (SWD) adults when exposed to the EF vapor released from an EF precursor after 2 h (A) and 4 h (B).

Example 10: Efficacy of EF Vapor Released from the Precursor on Mortality of Insects The EF precursor from Example 1 was activated using an acid-dispersed substrate (acidified substrate prepared in Example 1) and the moisture generated from fruit respiration to release EF vapor. In a model system utilized spotted-wing *Drosophila* (SWD), an invasive insect pest of many fruit crops, as the surrogate test organism. The mortality of adult SWD on blueberries was evaluated when they were exposed to the EF vapor released from the precursor. Different amounts of the EF precursor (2.5, 5.0, and 7.5 mg) were activated using the citric acid-dispersed substrate to release 1, 2, and 3 mg of EF, respectively, in a sealed 1 L glass jar containing 0, 20 or 40 g of blueberries and 10 adult SWD. Different degrees of mortality were observed for the insect depending on the EF concentrations and blueberries quantities (FIG. 12). After 2 h, 63% mortality was achieved for 1 mg EF, while 96% mortality was achieved for 3 mg EF for jar with 40 g of blueberries. Mortality was significantly ($p>0.05$) lower for jars without blueberries, where it was 16 and 60% for 1 and 3 mg EF, respectively. Mortality of 100% was achieved at all the concentrations at 4 h.

Figure 13:
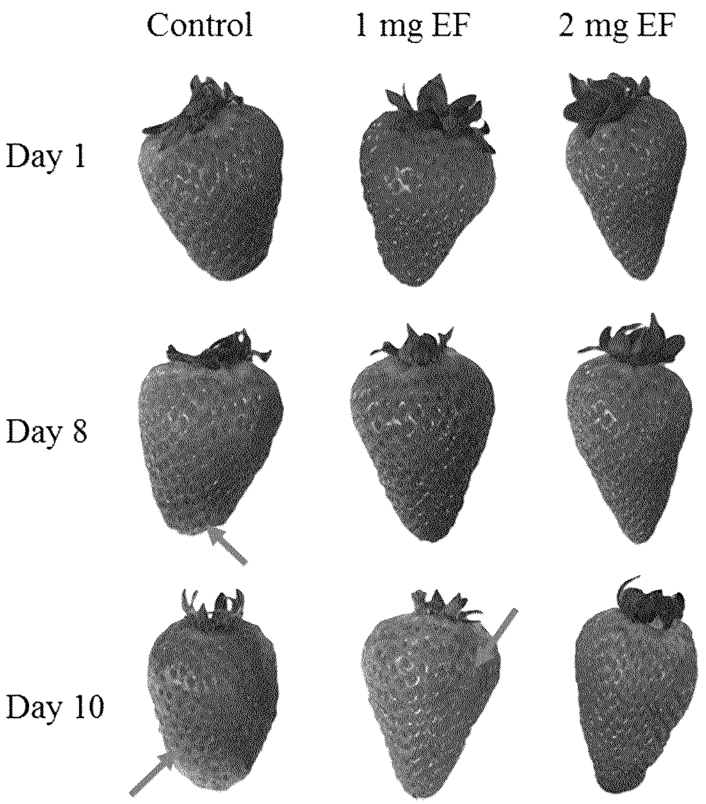
FIG. 13 are photographs of strawberries fumigated with 1 and 2 mg EF released from EC-PEO nonwoven loaded with a 70% EF precursor. Samples were stored in poly(ethylene terephthalate) (PET) packages for 10 days at 5° C., showing delayed mold growth for treated samples compared to the control.
Figure 14:
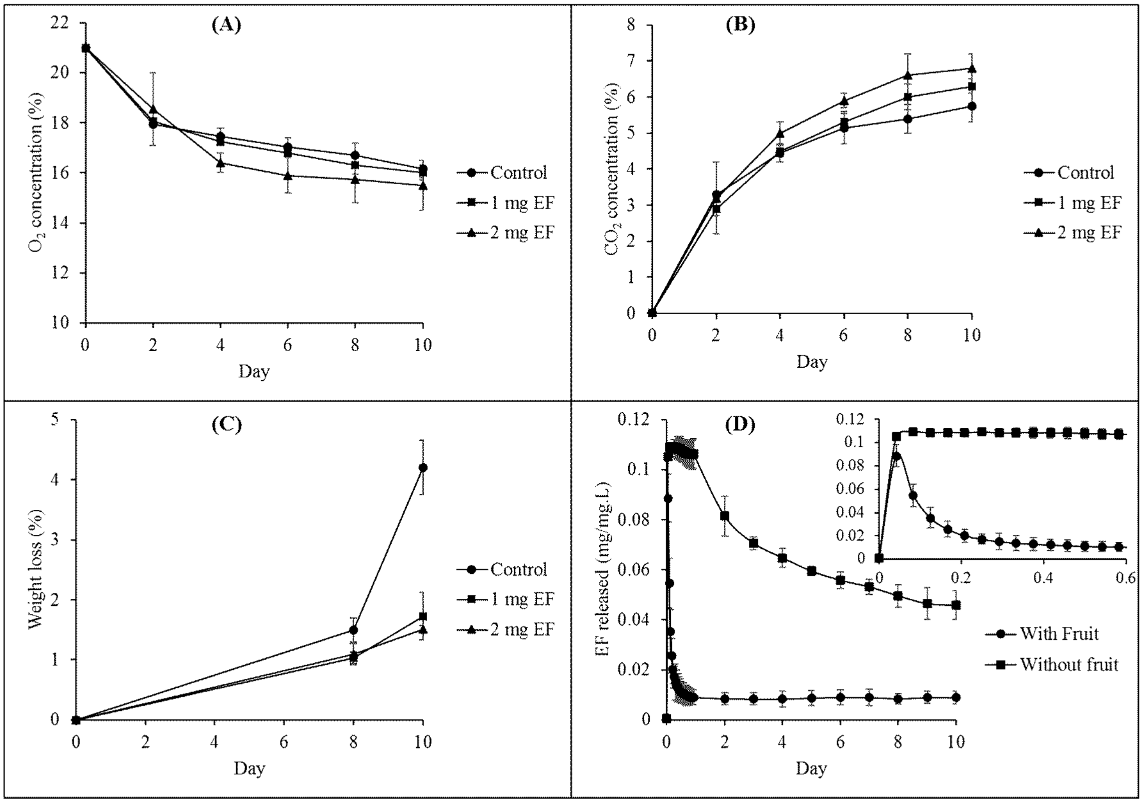
FIG. 14 shows the headspace 02 concentration (A), headspace $CO_2$ concentration (B), fruit weight loss percentages (C), and headspace EF concentration profiles inside PET packages for 10 days.

Example 11: The Efficacy of EF Release on Extending the Shelf-Life of Strawberries To illustrate the use of EF precursor for fruit preservation, preliminary tests of EF precursor-loaded nonwovens were performed to evaluate their ability to extend the shelf-life of strawberries packaged in thermoformed poly(ethylene terephthalate) (PET) packages (~80 g of strawberries). EF precursor-loaded nonwovens from Example 3 (8 and 16 mg; 70% precursor loading) were activated using 0.1 N CA solution to release approximately 1 and 2 mg of EF vapor (calculated based on the results from Table 3), respectively, inside the PET packages. FIG. 13 showed the appearance of strawberries after storage for 1, 8, 10 days at 5° C. (the arrows show areas of spoilage). The EF vapor released from the nonwovens considerably delayed the spoilage of strawberries. To evaluate the respiration behavior of the fruits, headspace $O_2$ and $CO_2$ concentrations were determined during storage. With 2 mg EF treatment, during the 10-day storage, the $O_2$ concentration declined gradually to 15.5±1% (FIG. 14A) while $CO_2$ concentration increased to 6.8±0.4% by day 10 (FIG. 14B). As shown in FIG. 14C, samples treated with 2 mg EF had the lowest weight loss, i.e., 1 and 1.5% on the 8th and 10th day, respectively. The control sample suffered the greatest weight loss. The EF release profiles in the package headspace (with/without fruits), were also measured for up to 10 days (FIG. 14D). For package without fruit, EF released rapidly, reaching a maximal concentration of 0.11±0.01 mg/mg·L after 20 h of nonwoven activation. The maximum level of EF remained for up to 24 h followed by a depletion to 0.05±0.01 mg/mg·L on 10th day. In the presence of fruit, the release of EF reached a peak level at 0.9±0.01 mg/mg·L after 1 h of activation, followed by a rapid decrease to 0.01±0.00 mg/mg·L within 24 h and stabilized at this level till the end of the experiment. These observations suggested that EF night have been degraded in the fruit to biogenic levels during storage.

While the present disclosure has been described with reference to what are presently considered to be the preferred examples, it is to be understood that the application is not limited to the examples described herein. To the contrary, the present disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

TABLE 1

EF released from the precursor (A and B) after 120 min at different temperatures using 0.1N citric acid, and the fitted model parameters. The unit "mg/mg · L" is referring to milligram of EF per milligram of precursor per litre of headspace air.

| | Temperature | EF released | | $C_e$ | k | |
|---|---|---|---|---|---|---|
| Precursor | ° C. | mg/mg · L | % | mg/mg · L | $min^{-1}$ | $R^2$ |
| A | 25 | 0.348 ± 0.006$^{a, b}$ | 89.0 ± 1.5 | 0.350 ± 0.005$^{a}$ | 0.037 ± 0.000$^{a}$ | 0.999 |
| B | 25 | 0.382 ± 0.008$^{a}$ | 97.9 ± 2.0 | 0.389 ± 0.007$^{a, b}$ | 0.030 ± 0.001$^{b}$ | 0.998 |
| B | 15 | 0.316 ± 0.013$^{b}$ | 81.1 ± 3.2 | 0.456 ± 0.014$^{a, b}$ | 0.010 ± 0.000$^{c}$ | 0.998 |
| B | 5 | 0.261 ± 0.011$^{c}$ | 66.8 ± 2.9 | 0.792 ± 0.004$^{c}$ | 0.004 ± 0.001$^{d}$ | 0.999 |

Different alphabets ($^{a-d}$) indicate statistical significant difference ($p < 0.05$) within each column.

TABLE 2

EF released from the precursor (B) at 25° C. after 120 min using different RH % with acidified paper, and the fitted model parameters. mg/mg · L is milligram of EF per milligram of precursor per litre of headspace air.

| RH | EF released | | $C_e$ | k | |
|---|---|---|---|---|---|
| % | mg/mg · L | % | mg/mg · L | $min^{-1}$ | $R^2$ |
| 94 | 0.315 ± 0.014$^{a}$ | 80.8 ± 3.5 | 0.333 ± 0.019$^{a}$ | 0.026 ± 0.002$^{a}$ | 0.990 |
| 75 | 0.178 ± 0.028$^{b}$ | 45.7 ± 7.1 | 0.200 ± 0.037$^{b}$ | 0.024 ± 0.004$^{a}$ | 0.994 |
| 53 | 0.037 ± 0.007$^{c}$ | 9.6 ± 1.8 | 0.072 ± 0.013$^{c}$ | 0.006 ± 0.001$^{b}$ | 0.979 |

TABLE 3

The EF released from its precursor embedded in EC-PEO electrospun fibers at 120 min and the fitted model parameters as affected by citric acid concentration, temperature, and EF precursor (EFP) loading capacity. The unit "mg/mg · L" is referring to milligram of EF per milligram of nonwoven per litre of headspace air.

| | Citric acid | Temp | EF released | | $C_e$ | k | |
|---|---|---|---|---|---|---|---|
| Nonwoven | solution | ° C. | mg/mg · L | % | mg/mg · L | $min^{-1}$ | $R^2$ |
| 10% EFP | 1N | 25 | 0.037 ± 0.001$^{a}$ | 95.9 ± 1.6 | 0.037 ± 0.000$^{a}$ | 0.109 ± 0.011$^{a}$ | 0.991 |
| 10% EFP | 0.1N | 25 | 0.037 ± 0.000$^{a, c}$ | 96.0 ± 0.7 | 0.037 ± 0.001$^{a, c}$ | 0.085 ± 0.004$^{a, b, d, f}$ | 0.994 |
| 10% EFP | 0.01N | 25 | 0.035 ± 0.001$^{a}$ | 89.3 ± 1.3 | 0.034 ± 0.001$^{a}$ | 0.055 ± 0.005$^{b, c}$ | 0.986 |

TABLE 3-continued

The EF released from its precursor embedded in EC-PEO electrospun fibers at 120 min and the fitted model parameters as affected by citric acid concentration, temperature, and EF precursor (EFP) loading capacity. The unit "mg/mg · L" is referring to milligram of EF per milligram of nonwoven per litre of headspace air.

| Nonwoven | Citric acid solution | Temp ° C. | EF released mg/mg · L | EF released % | $C_e$ mg/mg · L | k $min^{-1}$ | $R^2$ |
|---|---|---|---|---|---|---|---|
| 10% EFP | 0.001N | 25 | 0.029 ± 0.001[b] | 74.9 ± 2.0 | 0.042 ± 0.003[b] | 0.011 ± 0.001[c] | 0.982 |
| 10% EFP | 0.1N | 25 | 0.037 ± 0.000[a, c] | 96.0 ± 0.7 | 0.037 ± 0.001[a, c] | 0.085 ± 0.004[a, b, d, f] | 0.994 |
| 10% EFP | 0.1N | 15 | 0.034 ± 0.002[c, d] | 87.1 ± 5.1 | 0.033 ± 0.002[c, d] | 0.063 ± 0.005[d] | 0.991 |
| 10% EFP | 0.1N | 5 | 0.029 ± 0.001[d] | 76.0 ± 2.3 | 0.030 ± 0.001[d] | 0.031 ± 0.002[e] | 0.983 |
| 10% EFP | 0.1N | 25 | 0.037 ± 0.000[a, c] | 96.0 ± 0.7 | 0.037 ± 0.001[a, c] | 0.085 ± 0.004[a, b, d, f] | 0.994 |
| 30% EFP | 0.1N | 25 | 0.081 ± 0.002[e] | 91.1 ± 1.6 | 0.082 ± 0.003[e] | 0.071 ± 0.003[f, g] | 0.986 |
| 50% EFP | 0.1N | 25 | 0.115 ± 0.001[f] | 87.8 ± 0.3 | 0.116 ± 0.002[f] | 0.065 ± 0.002[f, g] | 0.991 |
| 70% EFP | 0.1N | 25 | 0.136 ± 0.002[g] | 83.2 ± 1.9 | 0.135 ± 0.002[g] | 0.051 ± 0.005[g] | 0.998 |
| 100% EFP | 0.1N | 25 | 0.146 ± 0.005[g] | 74.8 ± 2.8 | 0.145 ± 0.004[g] | 0.046 ± 0.001[g] | 0.993 |

Different alphabets ([a-g]) indicate statistical significant difference ($p < 0.05$) within each column for each effect (i.e., normality level, temperature, and EFP loading).

REFERENCES HEREIN INCORPORATED BY REFERENCE

ASTM Standard E104-02. 2012. "Standard Practice for Maintaining Constant Relative Humidity by Means of Aqueous Solutions." Www.Astm.Org. https://doi.org/10.1520/E0104-02R12.2.

Bessi, Haithem, Sihem Bellagha, Kaouthar Grissa Lebdi, Veronique Bikoba, and Elizabeth J. Mitcham. 2015. "Ethyl Formate Fumigation of Dry and Semidry Date Fruits: Experimental Kinetics, Modeling, and Lethal Effect on Carob Moth." Journal of Economic Entomology. https://doi.org/10.1093/jee/tov032.

Bolin, H R, A D King Jr, W L Stanley, and L Jurd. 1972. "Antimicrobial Protection of Moisturized Deglet Noor Dates." Applied and Environmental Microbiology.

Damcevski, K. A. ans Annis, P. C. 2006. Influence of grain and relative humidity on the mortality of Sitophilusorzae (L.) adults exposed to ethyl formate vapour. J. Stored Products Res. 42:61-74.

Desmarchelier, J M. 1999. "Ethyl Formate and Formic Acid: Occurrence and Environmental Fate." Postharvest News and Information 10: 7-12.

Günzler, H, and H-U Gremlich. 2002. IR Spectroscopy: An Introduction. Wiley-VCH, Weinheim.

Learmonth, Stewart, YongLin Ren, Manjree Agarwal, James Newman, Hui Cheng, and

John Sutton. 2012. "Evaluation of Ethyl Formate & Nitrogen for the Disinfestation of Eucalyptus Weevils on Export Apples." Department of Agriculture & Food, Western Australia, Murdoch University, Horticulture Australia Ltd PN #AP09045.

Lee, Laurence, Joseph Arul, Robert Lencki, and Francois Castaigne. 1995. "A Review on Modified Atmosphere Packaging and Preservation of Fresh Fruits and Vegetables: Physiological Basis and Practical Aspects—Part I." Packaging Technology and Science.

Pavia, D., Lampman, G., Kriz, G., Vyvyan, J. 2013. Introduction to Spectroscopy. Journal of Magnetic Resonance, Series A. https://doi.org/10.1006/jmra.1996.0145.

Petersen, Karina, Per Vggemose Nielsen, Grete Bertelsen, Mark Lawther, Mette B. Olsen, Nils H. Nilsson, and Grith Mortensen. 1999. "Potential of Biobased Materials for Food Packaging." Trends in Food Science and Technology. https://doi.org/10.1016/S0924-2244(99)00019-9.

Ragaert, P., F. Devlieghere, and J. Debevere. 2007. "Role of Microbiological and Physiological Spoilage Mechanisms during Storage of Minimally Processed Vegetables." Postharvest Biology and Technology. https://doi.org/10.1016/j.postharvbio.2007.01.001.

reenspan, Lewis. 1977. "Humidity Fixed Points of Binary Saturated Aqueous Solutions." Journal of Research of the National Bureau of Standards Section A: Physics and Chemistry. https://doi.org/10.6028/jres.081A.011.

Ren, Yong Lin, and Daphne Mahon. 2006. "Fumigation Trials on the Application of Ethyl Formate to Wheat, Split Faba Beans and Sorghum in Small Metal Bins." Journal of Stored Products Research. https://doi.org/10.1016/j.jspr.2005.04.002.

Schafer, K. S. 1999. "Methyl bromide phase-out strategies: A global compilation of the laws and regulations". United Nations Environment program.

Simpson, T, V Bikoba, C Tipping, and E J Mitcham. 2007. "Ethyl Formate as a Postharvest Fumigant for Selected Pests of Table Grapes." Journal of Economic Entomology. https://doi.org/10.1603/0022-0493(2007)100[1084:EFAAPF]2.0.CO; 2.

Simpson, Tiffanie, Veronique Bikoba, and Elizabeth J. Mitcham. 2004. "Effects of Ethyl Formate on Fruit Quality and Target Pest Mortality for Harvested Strawberries." Postharvest Biology and Technology 34 (3): 313-19. https://doi.org/10.1016/j.postharvbio.2004.05.015.

Utama, I. Made S., Ron B. H. Wills, Shimshon Ben-Yehoshua, and Clem Kuek. 2002. "In Vitro Efficacy of Plant Volatiles for Inhibiting the Growth of Fruit and Vegetable Decay Microorganisms." Journal of Agricultural and Food Chemistry. https://doi.org/10.1021/jf020484d.

The invention claimed is:

1. A compound of formula (I)

(I)

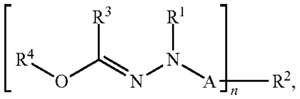

wherein

A is C═O, C═S, —S($O_2$)—, or —C═N—R, wherein R is H or $C_{1-5}$-alkyl;

$R^1$ is H, $C_1$-$C_5$-alkyl, or phenyl;

$R^2$ is a mono-, di-, tri- or tetra $C_1$-$C_{18}$-hydrocarbyl radical which is linear, branched, or cyclic, or a combination thereof;

$R^3$ is H or $C_1$-$C_3$-alkyl;

$R^4$ is $C_1$-$C_5$-alkyl or $C_6$-$C_{10}$-aryl;

n is the integer 1, 2, 3, or 4, wherein when n is 1, the compound of formula (I) has the structure (IA)

(IA)

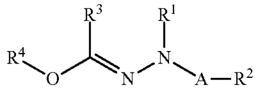

and $R^2$ is a $C_6$-$C_{18}$-alkyl group.

2. The compound of formula (I) of claim 1, wherein A is C═O.

3. The compound of formula (I) of claim 1, wherein $R^1$ is H, $C_1$-$C_3$-alkyl, or phenyl.

4. The compound of formula (I) of claim 3, wherein $R^1$ is H, or $C_1$-$C_3$-alkyl.

5. The compound of formula (I) of claim 4, wherein $R^1$ is H.

6. The compound of formula (I) of claim 1, wherein n is 2, and the compound of formula (I) has the structure (IB)

(IB)

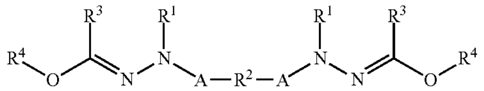

and $R^2$ is a $C_6$-$C_{10}$-alkylene or $C_6$-$C_{10}$ alkenylene group.

7. The compound of formula (I) of claim 1, wherein n is 3, and the compound of formula (I) has the structure (IC)

(IC)

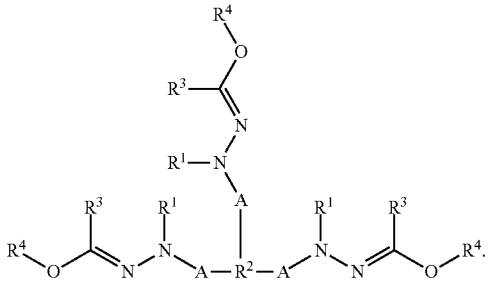

8. The compound of formula (I) of claim 1, wherein n is 4, and the compound of formula (I) has the structure (ID)

(ID)

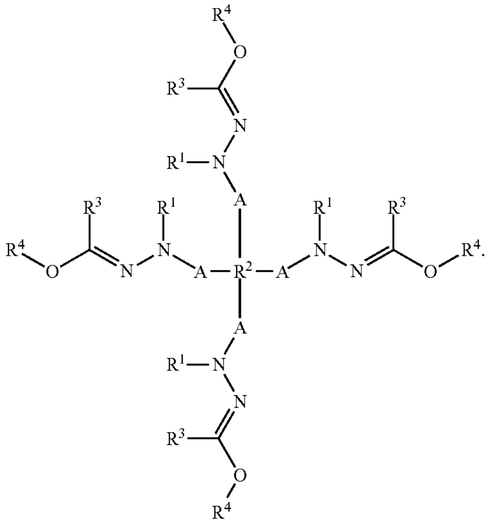

9. The compound of formula (I) of claim 1, wherein $R^3$ is H.

10. The compound of formula (I) of claim 1, wherein $R^4$ is $C_1$-$C_5$-alkyl or phenyl.

11. The compound of formula (I) of claim 10, wherein $R^4$ is $C_1$-$C_5$-alkyl.

12. The compound of formula (I) of claim 11, wherein $R^4$ is methyl or ethyl.

13. The compound of formula (I) of claim 1, wherein the compound releases a compound of formula (II) upon being exposed to hydrolytic conditions (II)

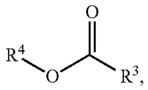

wherein $R^3$ is H or $C_1$-$C_3$-alkyl; and $R^4$ is $C_1$-$C_5$-alkyl or $C_6$-$C_{10}$-aryl.

* * * * *